(12) United States Patent
Oh et al.

(10) Patent No.: US 11,433,015 B2
(45) Date of Patent: Sep. 6, 2022

(54) PERSONAL CARE COMPOSITIONS COMPRISING ANTI-DANDRUFF AGENTS

(71) Applicant: The Procter & Gamble Company, Cincinnati, OH (US)

(72) Inventors: Hiroshi Oh, Cincinnati, OH (US); Dorothy A. Hall, Blanchester, OH (US); Steven Daryl Smith, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 30 days.

(21) Appl. No.: 17/016,868

(22) Filed: Sep. 10, 2020

(65) Prior Publication Data

US 2021/0069091 A1 Mar. 11, 2021

Related U.S. Application Data

(60) Provisional application No. 62/898,091, filed on Sep. 10, 2019.

(51) Int. Cl.
| | | |
|---|---|---|
| *A61Q 5/02* | (2006.01) | |
| *A61Q 19/10* | (2006.01) | |
| *A61K 8/81* | (2006.01) | |
| *A61K 8/23* | (2006.01) | |
| *A61K 8/49* | (2006.01) | |
| *A61K 8/89* | (2006.01) | |
| *A61Q 5/00* | (2006.01) | |
| *A61Q 5/12* | (2006.01) | |

(52) U.S. Cl.
CPC .............. *A61K 8/8158* (2013.01); *A61K 8/23* (2013.01); *A61K 8/4953* (2013.01); *A61K 8/89* (2013.01); *A61Q 5/006* (2013.01); *A61Q 5/02* (2013.01); *A61Q 5/12* (2013.01); *A61K 2800/412* (2013.01); *A61K 2800/5426* (2013.01); *A61K 2800/58* (2013.01); *A61K 2800/596* (2013.01); *A61K 2800/624* (2013.01)

(58) Field of Classification Search
None
See application file for complete search history.

(56) References Cited

U.S. PATENT DOCUMENTS

| | | |
|---|---|---|
| 2,809,971 A | 10/1957 | Bernstein |
| 3,236,733 A | 2/1966 | Karsten |
| 3,753,196 A | 8/1973 | Kurtz |
| 3,761,418 A | 9/1973 | Parran |
| 4,323,683 A | 4/1982 | Bolich, Jr. |
| 4,345,080 A | 8/1982 | Bolich, Jr. |
| 4,379,753 A | 4/1983 | Bolich, Jr. |
| 4,470,982 A | 9/1984 | Winkler |
| 5,104,646 A | 4/1992 | Bolich, Jr. |
| 5,106,609 A | 4/1992 | Bolich, Jr. |
| 5,723,112 A | 3/1998 | Bowser |
| 5,925,615 A | 7/1999 | Kern |
| 6,102,846 A | 8/2000 | Patton |
| 6,190,314 B1 | 2/2001 | Ark |
| 6,293,904 B1 | 9/2001 | Blazey |
| 6,306,077 B1 | 10/2001 | Prabhu |
| 6,309,342 B1 | 10/2001 | Blazey |
| 6,333,027 B1 | 12/2001 | Hopkins |
| 6,520,905 B1 | 2/2003 | Surve |
| 6,572,562 B2 | 6/2003 | Marshall |
| 6,798,898 B1 | 9/2004 | Fedorovskaya |
| 6,994,670 B2 | 2/2006 | Teicher |
| 8,435,501 B2 | 5/2013 | Peffly et al. |
| 8,475,777 B2 | 7/2013 | Rautschek |
| 8,491,877 B2 | 7/2013 | Schwartz |
| 8,524,262 B2 | 9/2013 | Roy |
| 8,560,045 B2 | 10/2013 | Burke |
| 8,980,239 B2 | 3/2015 | Staudigel |
| 9,272,164 B2 | 3/2016 | Johnson |
| 9,427,391 B2 | 8/2016 | Peffly |
| 9,662,291 B2 | 5/2017 | Johnson |
| 2002/0012646 A1 | 1/2002 | Royce |
| 2002/0077256 A1 | 6/2002 | Niemiec |
| 2002/0168327 A1 | 11/2002 | Bailey |

(Continued)

FOREIGN PATENT DOCUMENTS

| | | |
|---|---|---|
| CN | 101904908 | 12/2010 |
| EP | 0074819 A2 | 3/1983 |

(Continued)

OTHER PUBLICATIONS

"New hair care and skin care polymers from Ashland deliverimproved performance", Focus on Surfactants, Elsevier, Amsterdam, NL, vol. 2010, No. 6, Jun. 1, 2010 (Jun. 1, 2010 ), p. 4, XP027079457, ISSN: 1351-4210, DOI: 10.1016/S1351-4210(10)70138-4 [retrieved on Jun. 1, 2010].
PCT Search Report and Written Opinion for PCT/US2012/058990 dated Nov. 7, 2013.
PCT Search Report and Written Opinion for PCT/US2012/058909 dated Nov. 7, 2013.
PCT Search Report and Written Opinion for PCT/US2014/039706 dated Aug. 26, 2014.
PCT Search Report and Written Opinion for PCT/US2020/070518 dated Nov. 17, 2020.
All Office Actions, U.S. Appl. No. 13/646,272, filed Oct. 5, 2012.
All Office Actions, U.S. Appl. No. 13/646,300, filed Oct. 5, 2012.
All Office Actions, U.S. Appl. No. 14/284,930, filed May 22, 2014.
All Office Actions, U.S. Appl. No. 14/289,589, filed May 28, 2014.
All Office Actions, U.S. Appl. No. 15/004,284, filed Jan. 22, 2016.

(Continued)

*Primary Examiner* — Jyothsna A Venkat
(74) *Attorney, Agent, or Firm* — Linda M. Sivik

(57) ABSTRACT

A personal care composition comprises a personal care adjunct ingredient, an anti-dandruff agent, and cationic co-polymer disposed on an outer surface of the anti-dandruff agent. The cationic co-polymer has a viscosity of at least 0.09 poise and comprises monomers selected from the group consisting of acrylamide ("AAM"), dimethyl acrylamide ("DMAA"), acrylamidopropyl trimethylamonium chloride ("APTAC"), methacrylamidopropyl trimethylammonium chloride ("MAPTAC"), and combinations thereof.

3 Claims, No Drawings

(56) References Cited

U.S. PATENT DOCUMENTS

| | | |
|---|---|---|
| 2003/0108501 A1 | 6/2003 | Hofrichter |
| 2003/0139344 A1 | 7/2003 | Hung |
| 2003/0176303 A1 | 9/2003 | Niemiec |
| 2004/0057920 A1 | 3/2004 | Focht |
| 2004/0157754 A1 | 8/2004 | Geary |
| 2004/0157755 A1 | 8/2004 | Niemiec |
| 2004/0234484 A1 | 11/2004 | Peffly |
| 2006/0120988 A1* | 6/2006 | Bailey ................ A61Q 5/006 424/70.21 |
| 2006/0134049 A1 | 6/2006 | Keenan |
| 2006/0224077 A1 | 10/2006 | Pauly |
| 2006/0229505 A1 | 10/2006 | Mundt |
| 2007/0009463 A1 | 1/2007 | Niebauer |
| 2007/0207109 A1 | 9/2007 | Peffly |
| 2007/0276087 A1 | 11/2007 | Paul |
| 2008/0091098 A1 | 4/2008 | Burke |
| 2008/0131386 A1 | 6/2008 | Hahn |
| 2008/0206179 A1 | 8/2008 | Peffly |
| 2008/0206355 A1 | 8/2008 | Schwartz |
| 2009/0176674 A1 | 7/2009 | Peffly |
| 2010/0056430 A1 | 3/2010 | Lester |
| 2010/0249060 A1 | 9/2010 | Smith |
| 2011/0002868 A1 | 1/2011 | Bierganns |
| 2012/0016257 A1 | 1/2012 | Burke |
| 2013/0089586 A1 | 4/2013 | Johnson |
| 2013/0309283 A1 | 11/2013 | Rautschek |
| 2014/0348886 A1 | 11/2014 | Johnson |
| 2014/0357962 A1 | 12/2014 | Harrington |
| 2016/0287509 A1 | 10/2016 | Peffly |
| 2017/0252277 A1 | 9/2017 | Staudigel |
| 2018/0265827 A1 | 9/2018 | Oh et al. |
| 2019/0282466 A1 | 9/2019 | Oh et al. |

FOREIGN PATENT DOCUMENTS

| | | | |
|---|---|---|---|
| EP | 0136914 A2 | 4/1985 | |
| EP | 1437121 | 4/1985 | |
| JP | 4918918 | 5/1974 | |
| WO | 9966886 A1 | 12/1999 | |
| WO | WO-2013050241 A1 * | 4/2013 | ........... A61K 8/4946 |
| WO | 2019072515 A1 | 4/2019 | |

OTHER PUBLICATIONS

Engmann, J. et al. "Sgueeze Flow Theory and Applications to Rheometry: A Review" J. of Non-Newtonian Fluid Mechanics, 132 (2005) 1-27.

http://rocketnews24.com/2012/11/18/266,667/, "Itch is contagious just by watching others' scratching their body/nervous and more discriminating than those with negative thoughts."

Imokawa et al. ("Antimicrobial effect of pyrithione" in J. Soc. Cosmet. Chem., 33, 27-37 (Jan./Feb. 1982).

Lepilleur, Carole, et al. "Use of Statistical modeling to predict the effect of formulation composition on coacervation, silicone deposition, and conditioning sensory performance of Cationic Cassia Polymers" J. Cosmet Sci., 62, 161-177.

Morioka, H. et al. "Effects of Zinc on the New Preparation Method of Hydroxy Double Salts" Inorg. Chem. 1999, 38, 4211-6.

Papoiu et al., "Contagious itch in humans: a study of visual 'transmission' of itch in atopic dermatitis and healthy subjects", Feb. 27, 2011, British Journal of Dermatology, pp. 1299-1303.

* cited by examiner

PERSONAL CARE COMPOSITIONS COMPRISING ANTI-DANDRUFF AGENTS

FIELD OF THE INVENTION

The present invention relates to personal care compositions comprising anti-dandruff agents comprising cationic co-polymer disposed thereon, and methods of depositing anti-dandruff agents.

BACKGROUND OF THE INVENTION

Consumers often desire personal care products for the many benefits they may provide. For example, it is not uncommon for a consumer to have in their home shampoos, conditioners, body washes, deodorants, hand washes, shaving gels, and the like. Often, such consumer products also include anti-dandruff or anti-microbial benefit agents such as zinc pyrithion (ZPT), azoxystrobin, and sulfur. For years, anti-dandruff shampoos have been widely used to treat dandruff and clean hair and scalp, but there still remains a need for improved anti-dandruff shampoos. In general, anti-dandruff shampoos are formulated with anti-dandruff agents in combination with surfactants and aqueous systems that are intended to deposit the anti-dandruff agents on the scalp. The anti-dandruff agents can be insoluble particulates, such as zinc pyrithione, azoxystrobin and sulfur. Many anti-dandruff shampoos use higher amounts of cationic polymers with anionic surfactants to form a coacervate, which aids in the deposition of insoluble particulate agents. Though it is believed that increased deposition can be achieved by using polymers to form a coacervate, it is further believed that coacervates can effectively entrain the anti-dandruff agent, thereby limiting an ability of the anti-dandruff agent to interact with a target (e.g., fungi, bacteria, epidermis) and thus limiting its bioavailability. Consumers continue to desire a shampoo that delivers superior anti-dandruff efficacy, but current formulations have difficulty providing bioavailable anti-dandruff agents.

In addition, human health is impacted by many microbial entities or microbials such as germs, bacteria, fungi, yeasts, molds, viruses, or the like. For example, infection by microbial entities or microbials including various viruses and bacteria cause a wide variety of sicknesses and ailments. To reduce such infections, people frequently wash their skin with antimicrobial soaps. Antibacterial soaps typically include soaps in combination with one or more actives, for example, antimicrobial agents; which can be in the form of a bar of soap. When the skin is washed with an antimicrobial soap, such as a bar soap, the surfactant of the soap typically removes most of the microbial entities or microbials on the skin, while the antimicrobial agent deposits at least in part onto the skin to provide residual protection against subsequent invasion. As such, it is desirable to improve the properties of an antimicrobial agent and/or composition to provide improved benefits.

SUMMARY OF THE INVENTION

The present invention relates to a personal care composition comprising a personal care adjunct ingredient; an anti-dandruff agent; and cationic co-polymer disposed on an outer surface of the anti-dandruff agent, and wherein said cationic co-polymer has a formula:

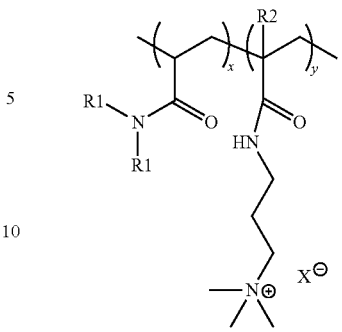

wherein
x is an integer selected such that the monomer units constitute less than 91% by weight of the cationic co-polymer;
y is an integer selected such that the monomer units constitute greater than 9% by weight of the cationic co-polymer;
each R1 is independently selected from the group consisting of H and $CH_3$;
each R2 is independently selected from the group consisting of H and $CH_3$; and
$X^-$ is a charge-balancing anion;
wherein said cationic co-polymer has a viscosity of at least 0.09 poise.

The present invention further relates to a method of depositing an anti-dandruff agent on a surface comprising the step of contacting the surface with a personal care composition of the present invention.

DETAILED DESCRIPTION OF THE INVENTION

The present invention relates to personal care compositions comprising a personal care adjunct ingredient, anti-dandruff agent, and cationic co-polymer disposed on the outer surface of the anti-dandruff agent.

Personal Care Compositions

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

All numerical parameters are to be understood as being prefaced and modified in all instances by the term "about" unless otherwise indicated. At the very least, and not as an attempt to limit the application of the doctrine of equivalents to the scope of the claims, each numerical parameter described herein should be construed in light of the number of reported significant digits and by applying ordinary rounding techniques.

Also, any numerical range recited herein is intended to include all sub-ranges of the same numerical precision subsumed within the recited range. For example, a range of "1.0 to 10.0" is intended to include all subranges including and between the recited minimum value of 1.0 and the recited maximum value of 10.0—that is, having a minimum value equal to or greater than 1.0 and a maximum value equal to or less than 10.0—such as, for example, 1.4 to 7.6 or 8.1 to 9.7. Any maximum numerical limitation in any numerical range recited in this specification is intended to include all lower numerical limitations subsumed therein; and any minimum numerical limitation in any numerical range recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that an amendment expressly reciting any such sub-range would comply with the requirements of 35 U.S.C. § 112(a).

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the personal care composition.

"Apply" or "application," as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Soluble" means at least about 0.1 g of solute dissolves in 100 ml of solvent, at 25° C. and 1 atm of pressure.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

As used herein, the term "fluid" includes liquids and gels.

As used herein, the articles including "a" and "an" when used in a claim, are understood to mean one or more of what is claimed or described.

As used herein, the word "or" when used as a connector of two or more elements is meant to include the elements individually and in combination; for example X or Y, means X or Y or both.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "personal care compositions" includes hair care compositions (such as shampoos, hair colorants, hair conditioners), body washes, moisturizing body washes, shower gels, skin cleansers, cleansing milks, shaving preparations, liquid hand cleansers, facial cleansers, and other surfactant-based liquid compositions, and Bar soap.

Personal care compositions may exist in different forms. For example, a personal care composition may be in a liquid form. Personal care compositions may also be in a solid form, like in a bar soap or a semi-solid form, like a paste or gel. Solid personal care compositions can be provided in different shapes and forms, like a rectangle, oval or square, and may be in a powder or pellet form, for example. Additionally, solid and semi-solid forms may be combined with a substrate to form an article as described in more detail in U.S. Patent Application Publication Numbers 2012/0246851; 2013/0043145; 2013/0043146; and 2013/0043147.

"Bar soap," as used herein, refers to compositions intended for topical application to a surface such as skin or hair to remove, for example, dirt, oil, and the like. Bar soaps can be rinse-off formulations, in which the product is applied topically to the skin or hair and then subsequently rinsed within minutes from the skin or hair with water. Bar soaps can also be wiped off using a substrate. Bar soaps can be in the form of a solid (e.g., non-flowing) bar soap intended for topical application to skin or can be in the form of a soft solid which is compliant to the body. Bar soaps can be wrapped in a substrate which remains about all or a portion of the bar during use.

Many personal care compositions are water-based. Water can be lost, i.e. evaporated, during a process of making a personal care composition, or subsequently, with water being absorbed by surrounding packaging (e.g. a cardboard carton), and the like. Thus, a personal care composition can also include materials that tend to bind the water such that the water can be maintained in the personal care composition at the desired levels. Examples of such materials can include carbohydrate structurants and humectants such as glycerin. However, it will be appreciated that a personal care composition can be anhydrous.

A variety of optional ingredients can also be added to a personal care composition. Such suitable ingredients can include, but are not limited to, structurants, humectants, fatty acids, inorganic salts, and other antimicrobial agents or actives.

Personal care compositions can also include hydrophilic structurants, such as carbohydrate structurants and gums. Some suitable carbohydrate structurants include raw starch (corn, rice, potato, wheat, and the like) and pregelatinized starch. Some suitable gums include carregeenan and xanthan gum. A personal care composition may include from about 0.1% to about 30%, from about 2% to about 25%, or from about 4% to about 20%, by weight of the personal care composition, of a carbohydrate structurant.

Personal care compositions can also include one or more humectants. Examples of such humectants can include polyhydric alcohols. Further, humectants such as glycerin can be included the personal care composition as a result of production or as an additional ingredient. For example, glycerin can be a by-product after saponification of the personal care composition. Including additional humectant can result in a number of benefits such as improvement in hardness of the personal care composition, decreased water activity of the personal care composition, and reduction of a weight loss rate of the personal care composition over time due to water evaporation.

Personal care compositions can include inorganic salts. Inorganic salts can help to maintain a particular water content or level of the personal care composition and improve hardness of the personal care composition. The inorganic salts can also help to bind the water in the personal care composition to prevent water loss by evaporation or other means. A personal care composition can optionally include from about 0.01% to about 15%, from about 1% to about 12%, or from about 2.5% to about 10.5%, by weight of the personal care composition, of inorganic salt. Examples of suitable inorganic salts include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

As noted herein, the personal care composition may include 2-Pyridinol-N-oxide materials. Such materials may be effective against gram-positive bacteria, for example, *Staphylococcus aureus*. Personal care compositions may also include one or more additional antibacterial agents that can serve to further enhance antimicrobial effectiveness of the personal care composition. For example, a personal care composition can include from about 0.001% to about 2%, from about 0.01% to about 1.5%, or from about 0.1% to about 1%, by weight of the personal care composition, of additional antibacterial agent(s). Examples of suitable antibacterial agents include carbanilides, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid, and other organic acids. Other antibacterial agents include p-chloro-m-xylenol (PCMX), 4-Isopropyl-m-cresol (IPMP), Zinc pyrithione (ZPT), Benzalkonium chloride (BZK), Didecyl dimethyl ammonium chloride (DDAC), Hinokitiol. Still other suitable antibacterial agents are described in U.S. Pat. No. 6,488,943.

Liquid Personal Care Compositions

Liquid personal care compositions may include an aqueous carrier, which can be present at a level of from about 5% to about 95%, or from about 60% to about 85%. The aqueous carrier may comprise water, or a miscible mixture of water and organic solvent. Non-aqueous carrier materials may also be employed.

Such personal care compositions may include one or more detersive surfactants. The detersive surfactant component can be included to provide cleaning performance to the product. The detersive surfactant component in turn comprises anionic detersive surfactant, zwitterionic or amphoteric detersive surfactant, or a combination thereof. A representative, non-limiting, list of anionic surfactants includes anionic detersive surfactants for use in the compositions can include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, monoethanolamine cocoyl sulfate, sodium tridecyl benzene sulfonate, sodium dodecyl benzene sulfonate, sodium cocoyl isethionate and combinations thereof. In one example, the anionic surfactant can be sodium lauryl sulfate or sodium laureth sulfate. The concentration of the anionic surfactant component in the product can be any amount sufficient to provide a desired cleaning and/or lather performance, and generally ranges from about 2% to about 50%.

Amphoteric detersive surfactants suitable for use in the personal care compositions are well known in the art, and include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic detersive surfactants suitable for use in the rinse-off personal care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants include betaines, one example of which is cocoamidopropyl betaine.

Personal care compositions may comprise one or more phases. Such personal care compositions can include a cleansing phase and/or a benefit phase (i.e., a single- or multi-phase composition). Each of a cleansing phase or a benefit phase can include various components. The cleansing phase and the benefit phase can be blended, separate, or a combination thereof. The cleansing phase and the benefit phase can also be patterned (e.g. striped).

The cleansing phase of a personal care composition can include at least one surfactant. The cleansing phase may be an aqueous structured surfactant phase and be present at from about 5% to about 20%, by weight of the personal care composition. Such a structured surfactant phase may include sodium trideceth(n) sulfate, hereinafter STnS, wherein n can define average moles of ethoxylation. For example, n can range from about 0 to about 3; from about 0.5 to about 2.7, from about 1.1 to about 2.5, from about 1.8 to about 2.2, or n can be about 2. When n is less than 3, STnS may provide improved stability, improved compatibility of benefit agents within the personal care compositions, and increased mildness of the personal care compositions, such described benefits of STnS are disclosed in U.S. patent application Ser. No. 13/157,665.

The cleansing phase can also comprise at least one of an amphoteric surfactant and a zwitterionic surfactant. Suitable amphoteric or zwitterionic surfactants (in addition to those cited herein) can include, for example, those described in U.S. Pat. Nos. 5,104,646 and 5,106,609.

A cleansing phase can comprise a structuring system. A structuring system can comprise, optionally, a non-ionic emulsifier, optionally, from about 0.05% to about 5%, by weight of the personal care composition, of an associative polymer; and an electrolyte.

The personal care composition can be optionally free of sodium lauryl sulfate, hereinafter SLS, and can comprise at least a 70% lamellar structure. However, the cleansing phase could comprise at least one surfactant, wherein the at least one surfactant includes SLS. Suitable examples of SLS are described in U.S. patent application Ser. No. 12/817,786.

As noted herein, personal care compositions can also include a benefit phase. The benefit phase can be hydrophobic and/or anhydrous. The benefit phase can also be substantially free of surfactant. A benefit phase can also include a benefit agent. In particular, a benefit phase can comprise from about 0.1% to about 50%, by weight of the personal care composition, of the benefit agent. The benefit phase may comprise less benefit agent, for example, from about 0.5% to about 20%, by weight of the personal care composition, of the benefit agent. Examples of suitable benefit agents can include petrolatum, glyceryl monooleate, mineral oil, natural oils, and mixtures thereof. Additional examples of benefit agents can include water insoluble or hydrophobic benefit agents. Other suitable benefit agents are described in U.S. patent application Ser. No. 13/157,665.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic skin benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

The personal care composition may be applied by a variety of means, including by rubbing, wiping or dabbing with hands or fingers, or by means of an implement and/or delivery enhancement device. Non-limiting examples of implements include a sponge or sponge-tipped applicator, a mesh shower puff, a swab, a brush, a wipe (e.g., wash cloth), a loofah, and combinations thereof. Non-limiting examples of delivery enhancement devices include mechanical, electrical, ultrasonic and/or other energy devices. Employment of an implement or device may help delivery of the particulate antimicrobial agent to target regions, such as, for example, hair follicles and undulations that can exist in the underarm. The personal care composition may be sold together with such an implement or device. Alternatively, an implement or device can be sold separately but contain indicium to indicate usage with a personal care composition. Implements and delivery devices can employ replaceable portions (e.g., the skin interaction portions), which can be sold separately or sold together with the personal care composition in a kit.

Solid Personal Care Compositions

As noted herein, personal care compositions may be solid in form. Solid compositions can take many forms like powder, pellets, bars, etc. These forms will generally be described herein as bar soap, but solid composition could be in another form or shape. One example of a bar soap personal care composition can include from about 0.1% to about 35%, by weight of the personal care composition, of water, from about 45% to about 99%, by weight of the personal care composition, of soap, and from about 0.01% to about 5%, by weight of the personal care composition, of a particulate antimicrobial agent. Another suitable antimicrobial bar soap can include, for example, from about 0.1% to about 30%, by weight of the personal care composition, of water, from about 40% to about 99%, by weight of the personal care composition, of soap, and from about 0.25% to about 3%, by weight of the personal care composition, of a particulate antimicrobial agent.

Bar soap compositions can be referred to as conventional solid (i.e. non-flowing) bar soap compositions. Some bar soap compositions comprise convention soap, while others contain synthetic surfactants, and still others contain a mix of soap and synthetic surfactant. Bar compositions may include, for example, from about 0% to about 95% of a surfactant, preferably from about 20% to about 95% of a surfactant. In one example, a bar soap composition may include, for example, from about 0% to about 45% of a synthetic anionic surfactant. An example of a suitable conventional soap can include milled toilet bars that are unbuilt (i.e. include about 5% or less of a water-soluble surfactant builder).

A personal care bar composition can include, for example from about 45% to about 99% or from about 50% to about 75%, by weight of the personal care composition, of soap. Such soaps can include a typical soap, i.e., an alkali metal or alkanol ammonium salt of an alkane- or alkene monocarboxylic acid. Sodium, magnesium, potassium, calcium, mono-, di- and tri-ethanol ammonium cations, or combinations thereof, can be suitable for a personal care composition. The soap included in a personal care composition can include sodium soaps or a combination of sodium soaps with from about 1% to about 25% ammonium, potassium, magnesium, calcium, or a mixture of these soaps. Additionally, the soap can be well-known alkali metal salts of alkanoic or alkenoic acids having from about 12 to about 22 carbon atoms or from about 12 to about 18 carbon atoms. Another suitable soap can be alkali metal carboxylates of alkyl or alkene hydrocarbons having from about 12 to about 22 carbon atoms. Additional suitable soap compositions are described in U.S. patent application Ser. No. 13/036,889.

A personal care composition can also include soaps having a fatty acid. For example, a bar soap composition could use from about 40% to about 95% of soluble alkali metal soap of $C_8$-$C_{24}$ or $C_{10}$-$C_{20}$ fatty acids. The fatty acid may, for example, have a distribution of coconut oil that can provide a lower end of a broad molecular weight range or a fatty acid distribution of peanut or grapeseed oil, or their hydrogenated derivatives, which can provide an upper end of the broad molecular weight range. Other such compositions can include a fatty acid distribution of tallow and/or vegetable oil. The tallow can include fatty acid mixtures that can typically have an approximate carbon chain length distribution of 2.5% $C_{14}$, 29% $C_{16}$, 23% $C_{18}$, 2% palmitoleic, 41.5% oleic, and 3% linoleic. The tallow can also include other mixtures with a similar distribution, such as fatty acids derived from various animal tallows and/or lard. In one example, the tallow can also be hardened (i.e., hydrogenated) such that some or all unsaturated fatty acid moieties can be converted to saturated fatty acid moieties.

Suitable examples of vegetable oil include palm oil, coconut oil, palm kernel oil, palm oil stearine, soybean oil, and hydrogenated rice bran oil, or mixtures thereof, since such oils can be among more readily available fats. One example of a suitable coconut oil can include a proportion of fatty acids having at least 12 carbon atoms of about 85%. Such a proportion can be greater when mixtures of coconut oil and fats such as tallow, palm oil, or non-tropical nut oils or fats can be used where principal chain lengths can be $C_{16}$ and higher. The soap included in a personal care composition can be, for example, a sodium soap having a mixture of about 67-68% tallow, about 16-17% coconut oil, about 2% glycerin, and about 14% water.

Soap included in a personal care composition can also be unsaturated in accordance with commercially acceptable standards. For example, a soap included in a personal care composition could include unsaturation in a range of from about 37% to about 45% of saponified material.

Soaps included in a personal care composition can be made, for example, by a classic kettle boiling process or modern continuous soap manufacturing processes wherein natural fats and oils such as tallow or coconut oil or their equivalents can be saponified with an alkali metal hydroxide using procedures well known to those skilled in the art. Soap can also be made by neutralizing fatty acids such as lauric ($C_{12}$), myristic ($C_{14}$), palmitic ($C_{16}$), or stearic ($C_{18}$) acids, with an alkali metal hydroxide or carbonate.

Soap included in a personal care composition could also be made by a continuous soap manufacturing process. The soap could be processed into soap noodles via a vacuum flash drying process. One example of a suitable soap noodle comprises about 67.2% tallow soap, about 16.8% coconut soap, about 2% glycerin, and about 14% water, by weight of the soap noodle. The soap noodles can then be utilized in a milling process to finalize a personal care composition.

Personal Care Compositions
Detersive Surfactant

The personal care composition may comprise greater than about 10% by weight of a surfactant system which provides cleaning performance to the composition; further the composition may comprise greater than 12% by weight of a surfactant system which provides cleaning performance to the composition. The surfactant system comprises an anionic surfactant and/or a combination of anionic surfactants and/or a combination of anionic surfactants and co-surfactants selected from the group consisting of amphoteric, zwitterionic, nonionic and mixtures thereof. Various examples and descriptions of detersive surfactants are set forth in U.S. Pat. No. 8,440,605; U.S. Patent Application Publication No. 2009/155383; and U.S. Patent Application Publication No. 2009/0221463, which are incorporated herein by reference in their entirety.

The personal care composition may comprise from about 10% to about 25%, from about 10% to about 18%, from about 10% to about 14%, from about 10% to about 12%, from about 11% to about 20%, from about 12% to about 20%, and/or from about 12% to about 18% by weight of one or more surfactants.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the personal care composition include ammonium lauryl sulfate, ammonium laureth sulfate, ammonium C10-15 pareth sulfate, ammonium C10-15 alkyl sulfate, ammonium C11-15 alkyl sulfate, ammonium decyl sulfate, ammonium deceth sulfate, ammonium undecyl sulfate, ammonium undeceth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, sodium C10-15 pareth sulfate, sodium C10-15 alkyl sulfate, sodium C11-15 alkyl sulfate, sodium decyl sulfate, sodium deceth sulfate, sodium undecyl sulfate, sodium undeceth sulfate, potassium lauryl sulfate, potassium laureth sulfate, potassium C10-15 pareth sulfate, potassium C10-15 alkyl sulfate, potassium C11-15 alkyl sulfate, potassium decyl sulfate, potassium deceth sulfate, potassium undecyl sulfate, potassium undeceth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. The anionic surfactant may be sodium lauryl sulfate or sodium laureth sulfate.

The composition of the present invention can also include anionic surfactants selected from the group consisting of:
a) $R_1O(CH_2CHR_3O)_ySO_3M$;
b) $CH_3(CH_2)_zCHR_2\ CH_2O(CH_2CHR_3O)_ySO_3M$; and
c) mixtures thereof,
where $R_1$ represents $CH_3(CH_2)_{10}$, $R_2$ represents H or a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not zero (0), and M is a monovalent or divalent, positively-charged cation.

Suitable anionic alkyl sulfates and alkyl ether sulfate surfactants include, but are not limited to, those having branched alkyl chains which are synthesized from C8 to C18 branched alcohols which may be selected from the group consisting of: Guerbet alcohols, aldol condensation derived alcohols, oxo alcohols, F-T oxo alcohols and mixtures thereof. Non-limiting examples of the 2-alkyl branched alcohols include oxo alcohols such as 2-methyl-1-undecanol, 2-ethyl-1-decanol, 2-propyl-1-nonanol, 2-butyl 1-octanol, 2-methyl-1-dodecanol, 2-ethyl-1-undecanol, 2-propyl-1-decanol, 2-butyl-1-nonanol, 2-pentyl-1-octanol, 2-pentyl-1-heptanol, and those sold under the tradenames LIAL® (Sasol), ISALCHEM® (Sasol), and NEODOL® (Shell), and Guerbet and aldol condensation derived alcohols such as 2-ethyl-1-hexanol, 2-propyl-1-butanol, 2-butyl-1-octanol, 2-butyl-1-decanol, 2-pentyl-1-nonanol, 2-hexyl-1-octanol, 2-hexyl-1-decanol and those sold under the tradename ISOFOL® (Sasol) or sold as alcohol ethoxylates and alkoxylates under the tradenames LUTENSOL XP® (BASF) and LUTENSOL XL® (BASF).

The anionic alkyl sulfates and alkyl ether sulfates may also include those synthesized from C8 to C18 branched alcohols derived from butylene or propylene which are sold under the trade names EXXAL™ (Exxon) and Marlipal® (Sasol). This includes anionic surfactants of the subclass of sodium trideceth-n sulfates (STnS), where n is between about 0.5 and about 3.5. Exemplary surfactants of this subclass are sodium trideceth-2 sulfate and sodium trideceth-3 sulfate. The composition of the present invention can also include sodium tridecyl sulfate.

The composition of the present invention can also include anionic alkyl and alkyl ether sulfosuccinates and/or dialkyl and dialkyl ether sulfosuccinates and mixtures thereof. The dialkyl and dialkyl ether sulfosuccinates may be a C6-15 linear or branched dialkyl or dialkyl ether sulfosuccinate. The alkyl moieties may be symmetrical (i.e., the same alkyl moieties) or asymmetrical (i.e., different alkyl moieties). Nonlimiting examples include: disodium lauryl sulfosuccinate, disodium laureth sulfosuccinate, sodium bistridecyl sulfosuccinate, sodium dioctyl sulfosuccinate, sodium dihexyl sulfosuccinate, sodium dicyclohexyl sulfosuccinate, sodium diamyl sulfosuccinate, sodium diisobutyl sulfosuccinate, linear bis(tridecyl) sulfosuccinate and mixtures thereof.

The personal care composition may comprise a co-surfactant. The co-surfactant can be selected from the group consisting of amphoteric surfactant, zwitterionic surfactant, non-ionic surfactant and mixtures thereof. The co-surfactant can include, but is not limited to, lauramidopropyl betaine, cocoamidopropyl betaine, lauryl hydroxysultaine, sodium lauroamphoacetate, disodium cocoamphodiacetate, cocamide monoethanolamide and mixtures thereof.

The personal care composition may further comprise from about 0.25% to about 15%, from about 1% to about 14%, from about 2% to about 13% by weight of one or more amphoteric, zwitterionic, nonionic co-surfactants, or a mixture thereof.

Suitable amphoteric or zwitterionic surfactants for use in the personal care composition herein include those which are known for use in shampoo or other personal care cleansing. Non-limiting examples of suitable zwitterionic or amphoteric surfactants are described in U.S. Pat. Nos. 5,104,646 and 5,106,609, which are incorporated herein by reference in their entirety.

Amphoteric co-surfactants suitable for use in the composition include those surfactants described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable amphoteric surfactant include, but are not limited to, those selected from the group consisting of: sodium cocaminopropionate, sodium cocaminodipropionate, sodium cocoamphoacetate, sodium cocoamphodiacetate, sodium cocoamphohydroxypropylsulfonate, sodium cocoamphopropionate, sodium cornamphopropionate, sodium lauraminopropionate, sodium lauroamphoacetate, sodium lauroamphodiacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphodiacetate, ammonium cocoamphohydroxypropylsulfonate, ammonium cocoamphopropionate, ammonium cornamphopropionate, ammonium lauraminopropionate, ammonium lauroamphoacetate, ammonium lauroamphodiacetate, ammonium lauroamphohydroxypropylsulfonate, ammonium lauroamphopropionate, ammonium lauriminodipropionate, triethanol amine cocaminopropionate, triethanolamine cocaminodipropionate, triethanolamine cocoamphoacetate, triethanolamine cocoamphohydroxypropylsulfonate, triethanolamine cocoamphopropionate, triethanolamine cornamphopropionate, triethanolamine lauraminopropionate, triethanolamine lauroamphoacetate, triethanolamine lauroamphohydroxypropylsulfonate, triethanolamine lauroamphopropionate, triethanolamine cornamphopropionate, triethanolamine lauriminodipropionate, cocoamphodipropionic acid, disodium caproamphodiacetate, disodium caproamphoadipropionate, disodium caprylamphodiacetate, disodium caprylamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof The composition may comprise a zwitterionic co-surfactant, wherein the zwitterionic surfactant is a derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant can be selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof.

The co-surfactant can be a non-ionic surfactant selected from the alkanolamides group including: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, PPG-2 Hydroxyethyl Isostearamide and mixtures thereof.

Non-limiting examples of other anionic, zwitterionic, amphoteric, and non-ionic additional surfactants suitable for use in the personal care composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

Cationic Polymers

The personal care composition may also comprise a cationic polymer. These cationic polymers can include at least one of (a) a cationic guar polymer, (b) a cationic non-guar galactomannan polymer, (c) a cationic tapioca polymer, (d) a synthetic, non-crosslinked, cationic polymer, which may or may not form lyotropic liquid crystals upon combination with the detersive surfactant (e) a cationic cellulose polymer. Additionally, the cationic polymer can be a mixture of cationic polymers.

The personal care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

The cationic polymer, may include but not limited to a cationic guar polymer, has a weight average Molecular weight of less than 2.2 million g/mol, or from about 150 thousand to about 2.2 million g/mol, or from about 200 thousand to about 2.2 million g/mol, or from about 300 thousand to about 1.2 million g/mol, or from about 750,000 thousand to about 1 million g/mol. The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.8 meq/g.

The cationic guar polymer may have a weight average Molecular weight of less than about 1.5 million g/mol, and has a charge density of from about 0.1 meq/g to about 2.5 meq/g. The cationic guar polymer may have a weight average molecular weight of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol. from about 150 thousand to about 800 thousand g/mol, or from about 200 thousand to about 700 thousand g/mol, or from about 300 thousand to about 700 thousand g/mol, or from about 400 thousand to about 600 thousand g/mol. The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.5 meq/g.

Suitable cationic guar polymers include cationic guar gum derivatives, such as guar hydroxypropyltrimonium chloride. The cationic guar polymer may be a guar hydroxypropyltrimonium chloride. Specific examples of guar hydroxypropyltrimonium chlorides include the Jaguar® series commercially available from Solvay, for example Jaguar® C-500, commercially available from Solvay. Jaguar® C-500 has a charge density of 0.8 meq/g and a molecular weight of 500,000 g/mol. Other suitable guar hydroxypropyltrimonium chloride are: guar hydroxypropyltrimonium chloride which has a charge density of about 1.3 meq/g and a molecular weight of about 500,000 g/mol and is available from Solvay as Jaguar® Optima. Other suitable guar hydroxypropyltrimonium chloride are: guar hydroxypropyltrimonium chloride which has a charge density of about 0.7 meq/g and a molecular weight of about 1,500,000 g/mol and is available from Solvay as Jaguar® Excel. Other suitable guar hydroxypropyltrimonium chloride are: guar hydroxypropyltrimonium chloride which has a charge density of about 1.1 meq/g and a molecular weight of about 500,000 g/mol and is available from ASI, a charge density of about 1.5 meq/g and a molecular weight of about 500,000 g/mole is available from ASI.

Other suitable guar hydroxypropyltrimonium chloride are: Hi-Care 1000, which has a charge density of about 0.7 meq/g and a Molecular weight of about 600,000 g/mole and is available from Solvay; N-Hance 3269 and N-Hance 3270, which have a charge density of about 0.7 meq/g and a molecular weight of about 425,000 g/mol and are available from ASI; N-Hance 3196, which has a charge density of about 0.8 meq/g and a molecular weight of about 1,100,000 g/mol and is available from ASI. AquaCat CG518 has a charge density of about 0.9 meq/g and a Molecular weight of about 50,000 g/mol and is available from ASI. BF-13, which is a borate (boron) free guar of charge density of about 1.1 meq/g and molecular weight of about 800,000 and BF-17, which is a borate (boron) free guar of charge density of about 1.7 5 meq/g and M. Wt. of about 800,000 both available from ASI.

The personal care compositions of the present invention may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non-Guar Galactomannan polymer derivatives of the present invention have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

The non-guar galactomannan polymer derivatives may have a M. Wt. from about 1,000 to about 10,000,000, and/or from about 5,000 to about 3,000,000.

The personal care compositions of the invention can also include galactomannan polymer derivatives which have a cationic charge density from about 0.5 meq/g to about 7 meq/g. The galactomannan polymer derivatives may have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Alternatively, the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a molecular weight of about 1,000 g/mol to about 10,000,000 g/mol, and/or from about 50,000 g/mol to about 1,000,000 g/mol, and/or from about 100,000 g/mol to about 900,000 g/mol, and/or from about 150,000 g/mol to about 400,000 g/mol and a cationic charge density from about 1 meq/g to about 5 meq/g, and/or from 2 meq/g to about 4 meq/g and can be derived from a *cassia* plant.

The personal care compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The cationically modified starch polymers disclosed herein have a percent of bound nitrogen of from about 0.5% to about 4%.

The cationically modified starch polymers for use in the personal care compositions can have a molecular weight about 850,000 g/mol to about 1,500,000 g/mol and/or from about 900,000 g/mol to about 1,500,000 g/mol.

The personal care compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

Suitable cationically modified starch for use in personal care compositions are available from known starch suppliers. Also suitable for use in personal care compositions are nonionic modified starch that can be further derivatized to a cationically modified starch as is known in the art. Other suitable modified starch starting materials may be quaternized, as is known in the art, to produce the cationically modified starch polymer suitable for use in personal care compositions.

Anionic Polymers

A personal care composition may also comprise one or more anionic polymers. Anionic polymers are polymers that contain anionic functional groups. Non-limited examples of anionic functional groups include carboxylate, sulfonate, sulfate, phosphonate, phosphate, nitrate and others. Anionic polymers can be homopolymers, that is, polymers constructed using one type of monomer, or copolymers, that is, polymers constructed using more than one type of monomer (including one or more monomers with anionic functional groups and/or other monomers that contain non-anionic functional groups). The personal care composition may comprise from about 0.1% to about 10% of an anionic polymer, from about 0.25% to about 8% of an anionic polymer, or from about 0.5% to about 5% of an anionic polymer, or from about 1% to about 5% of an anionic polymer or from about 1% to about 2.5% of an anionic polymer.

The anionic polymer may be a polyacrylate, or polyacrylamide polymer. The personal care composition may comprise anionic polymers that are homopolymers based on acrylic acid, methacrylic acid or other related derivatives, non-limiting examples include polyacrylate, polymethacrylate, polyethylacrylate, and polyacrylamide.

The anionic polymer may be alkali swellable and hydrophobically-modified alkali swellable acrylic copolymers or methacrylate copolymers, non-limiting examples include acrylic acid/acrylonitrogens copolymer, acrylates/steareth-20 itaconate copolymer, acrylates/ceteth-20 itaconate copolymer, Acrylates/Aminoacrylates/C10-30 Alkyl PEG-20 Itaconate Copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, Acrylates/Palmeth-25 Acrylate Copolymer, Acrylic Acid/Acrylamidomethyl Propane Sulfonic Acid Copolymer, and acrylates/C10-C30 alkyl acrylate crosspolymer.

The anionic polymer may be soluble crosslinked acrylic polymers, a non-limiting example includes carbomers.

The anionic polymer may be an associative polymer, non-limiting examples include: hydrophobically modified, alkali swellable emulsions, non-limiting examples include hydrophobically modified polypolyacrylates; hydrophobically modified polyacrylic acids, and hydrophobically modified polyacrylamides; hydrophobically modified polyethers wherein these materials may have a hydrophobe that can be selected from cetyl, stearyl, oleayl, and combinations thereof.

Non-limited examples of anionic polymers include: C-LC/SD-PC: Sodium Polyaspartate; Poly(2-acrylamido-2-methyl-1-propanesulfonic acid) which has a MW of about 2,000,000; Poly(2-acrylamido-2-methyl-1-propanesulfonic acid-co-acrylonitrile) acrylonitrile; Poly(4-styrenesulfonic acid-co-maleic acid) sodium salt which has a MW of about 20,000; PVM/MA Copolymer; FLEXAN® II Polymer: Sodium Polystyrene Sulfonate which has a MW of about 70,000 or 200,000 or 1,000,000; Polystyrene Sulfonate which has a MW of about 75,000; Ammonium Polystyrene Sulfonate which has a MW of about 200,000; MIRUSTYLE X-HP Sodium Laneth-40 Maleate/Styrene Sulfonate Copolymer; MIRUSTYLE X-HV Sodium Methoxy PEG-16 Maleate/Styrene Sulfonate Copolymer; Polyanetholesulfonic acid sodium salt; Covacryl MV 60: Sodium Polyacrylate which has a MW of about 2,100 or 5,100 or 8,000 or 15,000; Covacryl SP: Polyacrylic Acid; Poly(vinyl sulfate) potassium salt which has a MW of about 170,000; Poly(vinylsulfonic acid, sodium salt); EcoSmooth™ Satin: Ethylene/Sodium Acrylate Copolymer; Fixate™ Plus Polymer: Polyacrylate-14; Fixate™ Superhold Polymer: Polyacrylate-2 Crosspolymer; Fixomer™ A-30 Polymer: Methacrylic Acid (and) Methacrylic Acid/Sodium Acrylamidomethyl Propane Sulfonate Copolymer; Hyafactor™-PGA: Sodium Polyglutamate; Itaconix® DSP 2K™: Sodium Polyitaconate; Sodium Acrylate/Sodium Acryloyldimethyl Taurate Copolymer; Luviset® CA 66: VA/Crotonates Copolymer; Luviset® CAN: VA/Crotonates/Vinyl Neodecanoate Copolymer; Acrylates/Methacrylamide Copolymer; Carbomer; Sodium Carbomer; Rheocare® HSP-1180: Polyacrylamidomethylpropane Sulfonic Acid; Sodium Polynaphthalenesulfonate; Blanose™ cellulose gum purified sodium carboxymethylcellulose (CMC): Cellulose Gum; Aqualon® cellulose gum (CMC): Cellulose Gum; Fixate™ Design Polymer: Polyacrylate-32; Rhodicare® CFT: Xanthan Gum; Luviset® CAN: VA/Crotonates/Vinyl Neodecanoate Copolymer; Fixomer™ A-30 Polymer: Methacrylic Acid (and) Methacrylic Acid/Sodium Acrylamidomethyl Propane Sulfonate Copolymer; Fucogel®: Biosaccharide Gum-1; PECOSIL® PS-112: Dimethicone PEG-7 Phosphate; Ecopol-18S Anionic Guar: Carboxymethyl Hydroxypropyl Guar; Carrageenan; Sodium Carrageenan; Poly(methacrylic acid) with MW of about 100,000; Poly (ethyl acrylate/acrylic acid); Poly(methyl methacrylate/methacrylic acid) [90:10 monomer ratio] with MW of about 100,000; Poly(methyl methacrylate/methacrylic acid) [75:25 monomer ratio] with MW of about 1.2 million; Poly (methyl methacrylate/methacrylic acid) with MW of about 1.2 million 500,000; Poly(methyl methacrylate/methacrylic acid) [80:20 monomer ratio]; Poly(styrenesulfonic acid/maleic acid), sodium salt with MW of about 15,000; Poly (methacrylic acid) ammonium salt, 30% solution in water with MW of about 15,000; Poly(butadiene/maleic acid) 1:1, 42% soln. in water with MW of about 10,000-15,000; Poly(maleic acid), 50% soln. in water with MW of about 800-1200; Poly(vinylphosphonic acid), 30% Solution with MW of about 24,000; Poly(vinyl phosphoric acid), sodium salt with MW of about 200,000; Poly(vinylsulfonic acid) sodium salt, 25% solution in water with MW of about 4,000-6,000; Poly(acrylic acid), powder with MW of about 4,000,000; Poly(acrylic acid), 50% solution water with MW of about 5,000; Poly(acrylic acid), sodium salt, powder with MW of about 2,000; Poly(acrylic acid), sodium salt, 40% solution with MW of about 3,000; all available from Polysciences, Inc.

Thickening Polymers

A personal care composition may comprise a thickening polymer to increase the viscosity of the composition. Suitable thickening polymers can be used. The personal care composition may comprise from about 0.5% to about 10% of a thickening polymer, from about 0.8% to about 8% of a thickening polymer, from about 1.0% to about 5% of a thickening polymer, and about 1% to about 4% of a thickening polymer. The thickening polymer modifier may be a polyacrylate, polyacrylamide thickeners. The thickening polymer may be an anionic thickening polymer.

The personal care composition may comprise thickening polymers that are homopolymers based on acrylic acid, methacrylic acid or other related derivatives, non-limiting examples include polyacrylate, polymethacrylate, polyethylacrylate, and polyacrylamide.

The thickening polymers may be alkali swellable and hydrophobically-modified alkali swellable acrylic copolymers or methacrylate copolymers, non-limiting examples include acrylic acid/acrylonitrogens copolymer, acrylates/steareth-20 itaconate copolymer, acrylates/ceteth-20 itaconate copolymer, Acrylates/Aminoacrylates/C10-30 Alkyl PEG-20 Itaconate Copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, Acrylates/Palmeth-25 Acrylate Copolymer, Acrylic Acid/Acrylamidomethyl Propane Sulfonic Acid Copolymer, and acrylates/C10-C30 alkyl acrylate crosspolymer.

The thickening polymers may be soluble crosslinked acrylic polymers, a non-limiting example includes carbomers.

The thickening polymers may be an associative polymeric thickeners, non-limiting examples include: hydrophobically modified, alkali swellable emulsions, non-limiting examples include hydrophobically modified polyacrylates; hydrophobically modified polyacrylic acids, and hydrophobically modified polyacrylamides; hydrophobically modified polyethers wherein these materials may have a hydrophobe that can be selected from cetyl, stearyl, oleayl, and combinations thereof.

The thickening polymers may be used in combination with polyvinylpyrrolidone, crosslinked polyvinylpyrrolidone and derivatives. The thickening polymers may be combined with polyvinylalcohol and derivatives. The thickening polymers may be combined with polyethyleneimine and derivatives.

The thickening polymers may be combined with alginic acid based materials, non-limiting examples include sodium alginate, and alginic acid propylene glycol esters.

The thickening polymers may be used in combination with polyurethane polymers, non-limiting examples include: hydrophobically modified alkoxylated urethane polymers, non-limiting examples include PEG-150/decyl alcohol/SMDI copolymer, PEG-150/stearyl alcohol/SMDI copolymer, polyurethane-39.

The thickening polymers may be combined with an associative polymeric thickener, non-limiting examples include: hydrophobically modified cellulose derivatives; and a hydrophilic portion of repeating ethylene oxide groups with repeat units from 10-300, from 30-200, and from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

The thickening polymers may be combined with cellulose and derivatives, non-limiting examples include microcrystalline cellulose, carboxymethylcelluloses, hydroxyethylcellulose, hydroxypropylcellulose, hydroxypropyl methylcellulose, methylcellulose, ethyl cellulose; nitro cellulose; cellulose sulfate; cellulose powder; hydrophobically modified celluloses.

The thickening polymers may be combined with guar and guar derivatives, non-limiting examples include hydroxypropyl guar, and hydroxypropyl guar hydroxypropyl trimonium chloride.

The thickening polymers may be combined with polyethylene oxide; polypropylene oxide; and PEO-PPO copolymers.

The thickening polymers may be combined with polyalkylene glycols characterized by the general formula:

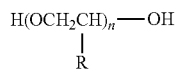

wherein R is hydrogen, methyl, or mixtures thereof, preferably hydrogen, and n is an integer having an average from 2,000-180,000, or from 7,000-90,000, or from 7,000-45,000. Non-limiting examples of this class include PEG-7M, PEG-14M, PEG-23M, PEG-25M, PEG-45M, PEG-90M, or PEG-100M.

The thickening polymers may be combined with silicas, non-limiting examples include fumed silica, precipitated silica, and silicone-surface treated silica.

The thickening polymers may be combined with water-swellable clays, non-limiting examples include laponite, bentolite, montmorilonite, smectite, and hectonite.

The thickening polymers may be combined with gums, non-limiting examples include xanthan gum, guar gum, hydroxypropyl guar gum, Arabia gum, tragacanth, galactan, carob gum, karaya gum, and locust bean gum.

The thickening polymers may be combined with, dibenzylidene sorbitol, karaggenan, pectin, agar, quince seed (*Cydonia oblonga* Mill), starch (from rice, corn, potato, wheat, etc), starch-derivatives (e.g. carboxymethyl starch, methylhydroxypropyl starch), algae extract, dextran, succinoglucan, and pulleran, Non--limiting examples of thickening polymers include acrylamide/ammonium acrylate copolymer (and) polyisobutene (and) polysorbate 20; acrylamide/sodium acryloyldimethyl taurate copolymer/isohexadecane/polysorbate 80, ammonium acryloyldimethyltaurate/VP copolymer, Sodium Acrylate/Sodium Acryloyldimethyl Taurate Copolymer, acrylates copolymer, Acrylates Crosspolymer-4, Acrylates Crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil; carbomer, sodium carbomer, crosslinked polyvinylpyrrolidone (PVP), polyacrylamide/C13-14 isoparaffin/laureth-7, polyacrylate 13/polyisobutene/polysorbate 20, polyacrylate crosspolymer-6, polyamide-3, polyquaternium-37 (and) hydrogenated polydecene (and) trideceth-6, Acrylamide/Sodium Acryloyldimethyltaurate/Acrylic Acid Copolymer, sodium acrylate/acryloyldimethyltaurate/dimethylacrylamide, crosspolymer (and) isohexadecane (and) polysorbate 60, sodium polyacrylate. Exemplary commercially-available thickening polymers include ACULYN™ 28, ACULYN™ 33, ACULYN™ 88, ACULYN™22, ACULYN™ Excel, Carbopol® Aqua SF-1, Carbopol® ETD 2020, Carbopol® Ultrez 20, Carbopol® Ultrez 21, Carbopol® Ultrez 10, Carbopol® Ultrez 30, Carbopol® 1342, Carbopol® Aqua SF-2 Polymer, Sepigel™ 305, Simulgel™ 600, Sepimax Zen, Carbopol® SMART 1000, Rheocare® TTA, Rheomer® SC-Plus, STRUCTURE® PLUS, Aristoflex® AVC, Stabylen 30 and combinations thereof.

Gel Network

In the present invention, a gel network may be present. The gel network component of the present invention may comprise at least one fatty amphiphile. As used herein, "fatty amphiphile" refers to a compound having a hydrophobic tail group as defined as an alkyl, alkenyl (containing up to 3 double bonds), alkyl aromatic, or branched alkyl group of $C_{12}$-$C_{70}$ length and a hydrophilic head group which does not make the compound water soluble, wherein the compound also has a net neutral charge at the pH of the shampoo composition.

Personal Care compositions of the present invention comprise fatty amphiphile as part of the pre-formed dispersed gel network phase in an amount from about 0.05% to about 14%, preferably from about 0.5% to about 10%, and more preferably from about 1% to about 8%, by weight of the personal care composition.

According to the present invention, suitable fatty amphiphiles, or suitable mixtures of two or more fatty amphiphiles, have a melting point of at least about 27° C. The melting point, as used herein, may be measured by a standard melting point method as described in U.S. Pharmacopeia, USP-NF General Chapter <741>"Melting range or temperature". The melting point of a mixture of two or more materials is determined by mixing the two or more materials at a temperature above the respective melt points and then allowing the mixture to cool. If the resulting composite is a homogeneous solid below about 27° C., then the mixture has a suitable melting point for use in the present invention. A mixture of two or more fatty amphiphiles, wherein the mixture comprises at least one fatty amphiphile having an individual melting point of less than about 27° C., still is suitable for use in the present invention provided that the composite melting point of the mixture is at least about 27° C.

Suitable fatty amphiphiles of the present invention include fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty acids, alkoxylated fatty acids, fatty diesters, fatty sorbitan esters, fatty sugar esters, methyl glucoside esters, fatty glycol esters, mono, di & tri glycerides, polyglycerine fatty esters, alkyl glyceryl ethers, propylene glycol fatty acid esters, cholesterol, ceramides, fatty silicone waxes, fatty glucose amides, and phospholipids and mixtures thereof.

In the present invention, the personal care composition may comprise fatty alcohol gel networks. These gel networks are formed by combining fatty alcohols and surfactants in the ratio of from about 1:1 to about 40:1, from about 2:1 to about 20:1, and/or from about 3:1 to about 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. The gel network contributes a stabilizing benefit to cosmetic creams and hair conditioners. In addition, they deliver conditioned feel benefits for hair conditioners.

The fatty alcohol can be included in the fatty alcohol gel network at a level by weight of from about 0.05 wt % to about 14 wt %. For example, the fatty alcohol may be present in an amount ranging from about 1 wt % to about 10 wt %, and/or from about 6 wt % to about 8 wt %.

The fatty alcohols useful herein include those having from about 10 to about 40 carbon atoms, from about 12 to about 22 carbon atoms, from about 16 to about 22 carbon atoms, and/or about 16 to about 18 carbon atoms. These fatty alcohols can be straight or branched chain alcohols and can be saturated or unsaturated. Nonlimiting examples of fatty alcohols include cetyl alcohol, stearyl alcohol, behenyl alcohol, and mixtures thereof. Mixtures of cetyl and stearyl alcohol in a ratio of from about 20:80 to about 80:20 are suitable.

Water Miscible Solvents

The carrier useful in a personal care composition may include water and water solutions of lower alkyl alcohols, polyhydric alcohols, ketones having from 3 to 4 carbons atoms, C1-C6 esters of C1-C6 alcohols, sulfoxides, amides, carbonate esters, ethoxylated and propoxylated C1-C10 alcohols, lactones, pyrollidones, and mixtures thereof. Non-limited lower alkyl alcohol examples are monohydric alcohols having 1 to 6 carbons, such as ethanol and isopropanol.

Non-limiting examples of polyhydric alcohols useful herein include propylene glycol, dipropylene glycol, butylenes glycol, hexylene glycol, glycerin, propane diol and mixtures thereof.

The personal care composition may comprise a hydrotrope/viscosity modifier which is an alkali metal or ammonium salt of a lower alkyl benzene sulphonate such as sodium xylene sulphonate, sodium cumene sulphonate or sodium toluene sulphonate.

In the present invention, a personal care composition may comprise silicone/PEG-8 silicone/PEG-9 silicone/PEG-n silicone/silicone ether (n could be another integer), non-limiting examples include PEG8-dimethicone A208) MW 855, PEG 8 Dimethicone D208 MW 2706.

Propellant or Blowing Agent

The personal care composition described herein may comprise from about from about 1% to about 10% propellant or blowing agent, alternatively from about 2% to about 8% propellant, by weight of the personal care composition.

The propellant or blowing agent may comprise one or more volatile materials, which in a gaseous state, may carry the other components of the personal care composition in particulate or droplet form or as a foam. The propellant or blowing agent may have a boiling point within the range of from about −45° C. to about 5° C. The propellant or blowing agent may be liquefied when packaged in convention aerosol containers under pressure. The rapid boiling of the propellant or blowing agent upon leaving the aerosol foam dispenser may aid in the atomization or foaming of the other components of the personal care composition.

Aerosol propellants or blowing agents which may be employed in an aerosol composition of the present invention may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and mixtures thereof. The propellant or blowing agent may comprise hydrocarbons such as isobutane, propane, and butane—these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar.

Optional Ingredients

In the present invention, a personal care composition may further comprise one or more optional ingredients, including benefit agents. Suitable benefit agents include, but are not limited to conditioning agents, cationic polymers silicone emulsions, anti-dandruff agents, gel networks, chelating agents, and natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof. In the present invention, the composition may have from about 0.5% to about 7% of a perfume.

Such optional ingredients should be physically and chemically compatible with the components of the composition, and should not otherwise unduly impair product stability, aesthetics, or performance The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

Conditioning Agents

The conditioning agent of a personal care composition of the present invention can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference.

The silicone conditioning agents for use in the compositions of the present invention can have a viscosity, as measured at 25° C., from about 20 to about 2,000,000 centistokes ("csk"), from about 1,000 to about 1,800,000 csk, from about 10,000 to about 1,500,000 csk, and/or from about 20,000 to about 1,500,000 csk.

The dispersed silicone conditioning agent particles typically have a volume average particle diameter ranging from about 0.01 micrometer to about 60 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the present invention include, but are not limited to, emulsions of insoluble polysiloxanes. These may be prepared via emulsion polymerization, as in accordance with the descriptions provided in U.S. Pat. No. 6,316,541 or 4,476,282 or U.S. Patent Application Publication No. 2007/0276087, or they may be emulsified after polymerization is complete, via a variety of emulsification methods as described in U.S. Pat. No. 9,255,184B2 or 7,683,119 or *Emulsions and Emulsion Stability*, edited by Johan Sjoblom, CRC Press, 2005. These references can be consulted for a non-limiting list of suitable emulsifiers and emulsifier blends based on the functionality of silicone used, the emulsification method, and the desired emulsion particle size. Accordingly, suitable insoluble polysiloxanes include polysiloxanes such as alpha, omega hydroxy-terminated polysiloxanes or alpha, omega alkoxy-terminated polysiloxanes having an internal phase viscosity from about 5 csk to about 500,000 csk. For example, the insoluble polysiloxane may have an internal phase viscosity less 400,000 csk, preferably less than 200,000 csk, more preferably from about 10,000 csk to about 180,000 csk. The insoluble polysiloxane can have an average particle size within the range from about 10 nm to about 10 micron. The average particle size may be within the range from about 15 nm to about 5 micron, from about 20 nm to about 1 micron, or from about 25 nm to about 550 nm or from about 1 to 10 micron. The concentration of dispersed silicone in the emulsion may be within the range from about 5 to 90 percent, or from 20 to 85 percent, or from 30 to 80 percent by weight of the emulsion composition.

The average molecular weight of the insoluble polysiloxane, the internal phase viscosity of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

The conditioning agent of the personal care compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Emulsifiers

A variety of anionic and nonionic emulsifiers can be used in personal care compositions of the present invention. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

Chelating Agents

Personal care compositions of the present invention can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Chelating agents can be incorporated in the compositions herein in amounts ranging from 0.001% to 10.0% by weight of the total composition, preferably 0.01% to 2.0%.

Nonlimiting chelating agent classes include carboxylic acids, aminocarboxylic acids, including aminocids, phosphoric acids, phosphonic acids, polyphosphonic acids, polyethyleneimines, polyfunctionally-substituted aromatic, their derivatives and salts.

Nonlimiting chelating agents include the following materials and their salts. Ethylenediaminetetraacetic acid (EDTA), ethylenediaminetriacetic acid, ethylenediamine-N,N'-disuccinic acid (EDDS), ethylenediamine-N,N'-diglutaric acid (EDDG), salicylic acid, aspartic acid, glutamic acid, glycine, malonic acid, histidine, diethylenetriaminepentaacetate (DTPA), N-hydroxyethylethylenediaminetriacetate, nitrilotriacetate, ethylenediaminetetrapropionate, triethylenetetraaminehexaacetate, ethanoldiglycine, propylenediaminetetracetic acid (PDTA), methylglycinediacetic acid (MODA), diethylenetriaminepentaacetic acid, methylglycinediacetic acid (MGDA), N-acyl-N,N',N'-ethylenediaminetriacetic acid, nitrilotriacetic acid, ethylenediaminediglutaric acid (EDGA), 2-hydroxypropylenediamine disuccinic acid (HPDS), glycinamide-N, N-disuccinic acid (GADS), 2-hydroxypropylenediamine-N—N'-disuccinic acid (HPDDS), N-2-hydroxyethyl-N,N-diacetic acid, glyceryliminodiacetic acid, iminodiacetic acid-N-2-hydroxypropyl sulfonic acid, aspartic acid N-carboxymethyl-N-2-hydroxypropyl-3-sulfonic acid, alanine-N,N'-diacetic acid, aspartic acid-N,N'-diacetic acid, aspartic acid N-monoacetic acid, iminodisuccinic acid, di amine-N,N'-dipoly acid, mono amide-N,N'-dipolyacid, diaminoalkyldi(sulfosuccinic acids) (DDS), ethylenediamine-N—N-bis (ortho-hydroxyphenyl acetic acid)), N,N'-bis(2-hydroxybenzyl)ethylenediamine-N, N-diacetic acid, ethylenediaminetetraproprionate, triethylenetetraaminehexacetate, diethylenetriaminepentaacetate, dipicolinic acid, ethylenedicysteic acid (EDC), ethylenediamine-N,N'-bis(2-hydroxyphenylacetic acid) (EDDHA), glutamic acid diacetic acid (GLDA), hexadentateaminocarboxylate (HBED), polyethyleneimine, 1-hydroxydiphosphonate, aminotri(methylenephosphonic acid) (ATMP), nitrilotrimethylenephosphonate (NTP), ethylenediaminetetramethylenephosphonate, diethylenetriaminepentamethylenephosphonate (DTPMP), ethane-1-hydroxydiphosphonate (HEDP), 2-phosphonobutane-1,2,4-tricarboxylic acid, polyphosphoric acid, sodium tripolyphosphate, tetrasodium diphosphate, hexametaphosphoric acid, sodium metaphosphate, phosphonic acid and derivatives, Aminoalkylen-poly (alkylenphosphonic acid), aminotri(1-ethylphosphonic acid), ethylenediaminetetra(1-ethylphosphonic acid), aminotri(1-propylphosphonic acid), aminotri(isopropylphosphonic acid), ethylenediaminetetra(methylenephosphonic acid) (EDTMP), 1,2-dihydroxy-3,5-disulfobenzene.

Aqueous Carrier

Personal care compositions of the present invention can be in the form of pourable liquids (under ambient conditions). Such compositions will therefore typically comprise a carrier, which is present at a level of from about 40% to about 85%, alternatively from about 45% to about 80%, alternatively from about 50% to about 75% by weight of the personal care composition. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful the personal care compositions of the present invention may include water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Foam Dispenser

A personal care composition of the present invention described herein may be provided in a foam dispenser. The foam dispenser may be an aerosol foam dispenser. The aerosol foam dispenser may comprise a reservoir for holding the personal treatment composition. The reservoir may be made out of any suitable material selected from the group consisting of plastic, metal, alloy, laminate, and combinations thereof. And the reservoir may be for one-time use. The reservoir may be removable from the aerosol foam dispenser. Alternatively, the reservoir may be integrated with the aerosol foam dispenser. And there may be two or more reservoirs.

The foam dispenser may also be a mechanical foam dispenser. The mechanical foam dispenser described may be selected from the group consisting of squeeze foam dispensers, pump foam dispensers, other mechanical foam dispensers, and combinations thereof. The mechanical foam dispenser may be a squeeze foam dispenser. Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

The mechanical foam dispenser may comprise a reservoir for holding the personal treatment composition. The reservoir may be made out of any suitable material selected from the group consisting of plastic, metal, alloy, laminate, and combinations thereof. The reservoir may be a refillable reservoir such as a pour-in or screw-on reservoir, or the reservoir may be for one-time use. The reservoir may also be removable from the mechanical foam dispenser. Alternatively, the reservoir may be integrated with the mechanical foam dispenser. And there may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

Product Form

The personal care compositions of the present invention may be presented in typical personal care formulations. They may be in the form of solutions, dispersion, emulsions, powders, talcs, encapsulated, spheres, spongers, solid dosage forms, foams, and other delivery mechanisms. The compositions the present invention may be hair tonics, leave-on hair products such as treatment, and styling products, rinse-off hair products such as shampoos and conditioners and personal cleansing products, and treatment products; and any other form that may be applied to hair.

Applicator

In the present invention, personal care composition may be dispensed from an applicator for dispensing directly to the scalp area. Dispensing directly onto the scalp via a targeted delivery applicator enables deposition of the non-diluted cleaning agents directly where the cleaning needs are highest. This also minimizes the risk of eye contact with the cleansing solution.

The applicator is attached or can be attached to a bottle containing the cleansing personal care composition. The applicator can consist of a base that holds or extends to a single or plurality of tines. The tines have openings that may be at the tip, the base or at any point between the tip and the base. These openings allow for the product to be distributed from the bottle directly onto the hair and/or scalp.

Alternatively, the applicator can also consist of brush-like bristles attached or extending from a base. In this case product would dispense from the base and the bristles would allow for product distribution via the combing or brushing motion.

Applicator and tine design and materials can also be optimized to enable scalp massage. In this case it would be beneficial for the tine or bristle geometry at the tips to be more rounded similar to the roller ball applicator used for eye creams. It may also be beneficial for materials to be smoother and softer; for example, metal or metal-like filaments.

EXAMPLES

The following examples are given solely for the purpose of illustration and are not to be construed as limitations of the present invention, as many variations thereof are possible without departing from the spirit and scope of the invention.

The compositions illustrated in the following examples are prepared by conventional formulation and mixing methods. All exemplified amounts are based on weight unless otherwise specified; and are listed as weight percentages on an active basis and exclude minor materials, such as diluents, preservatives, color solutions, imagery ingredients, botanicals, and so forth, unless otherwise specified. It will be appreciated that other modifications of Shampoo, bar soap and liquid soap compositions within the skill of those in the formulation art can be undertaken without departing from the spirit and scope of this invention.

TABLE 1

Shampoo Examples

| Ingredients | Examples, active wt % | | | | |
|---|---|---|---|---|---|
| | 1 | 2 | 3 | 4 | 5 |
| Water | q.s. to 100 | q.s. to 100 | q.s. to 100 | q.s. to 100 | q.s. to 100 |
| Sodium Laureth-1 Sulfate (SLE1S) [1] | 15.0 | 14.0 | 7.5 | 7.5 | 9.0 |
| Sodium Laureth-3 Sulfate (SLE3S) [2] | | | 7.5 | | |
| Sodium Decyl Sulfate [3] | | | | 7.5 | 4.0 |
| Cocamidopropyl Betaine (CAPB) [4] | | | | | 1.0 |
| Cocamide MEA (CMEA) [5] | | | | | 0.9 |
| Zinc Pyrithion [6] | 1.0 | 1.0 | 1.0 | 1.0 | 1.0 |
| Acrylates Copolymer [7] | | | | 2.5 | |
| Guar Hydroxypropyltrimonium Chloride [8] | | | 0.4 | 0.4 | |
| Sodium Benzoate [9] | 0.25 | 0.25 | 0.25 | 0.25 | 0.25 |
| Tetrasodium EDTA [10] | 0.13 | 0.13 | 0.13 | 0.13 | 0.13 |
| Methylchloroisothiazolinone/ Methylisothiazolinone [11] | 5 ppm | 5 ppm | 5 ppm | 5 ppm | 5 ppm |
| Citric Acid [12] | 0.60 | 0.47 | 0.32 | 0.32 | 0.31 |
| Fragrance | 0.85 | 0.85 | 1.0 | 1.0 | 0.85 |
| Sodium Chloride [13] | 1.0 | 1.0 | 0.26 | 0.26 | 1.0 |

[1] Sodium Laureth-1 Sulfate at 26% active, supplier: P&G
[2] Sodium Laureth-3 Sulfate at 28% active, supplier: P&G
[3] Sodium Decyl Sulfate at 27% active, supplier: P&G
[4] Tego Betain L 7 OK at 30% active, supplier: Evonik
[5] Ninol Comf at 85% active, supplier: Stepan
[6] Zinc Pyrithion: Arch Chemicals
[7] Carbopol Aqua SF-1 at 30% active, supplier: Lubrizol
[8] N-Hance BF-17, supplier: Ashland Specialty Ingredients
[9] Sodium Benzoate Dense NF/FCC, supplier: Emerald Performance Materials
[10] Dissolvine 220-S at 84% active, supplier: Akzo Nobel
[11] Kathon CG at 1.5% active, supplier: Rohm & Haas
[12] Citric Acid Anhydrous, supplier: Archer Daniels Midland; level adjustable to achieve target pH
[13] Sodium Chloride, supplier: Morton; level adjustable to achieve target viscosity Bar soap compositions of the present invention can be made via a number of different processes known in the art. Preferably, the present compositions are made via a milling process, resulting in milled bar soap compositions. A typical milling process of manufacturing a bar soap composition includes: (a) a step in which the soap is made through either a continuous process (ConSap or continuous saponification process) or a batch-making process (i.e. neutralization process for hydrolysis fatty acid noodle or kettle process), (b) a vacuum drying step in which the soap is made into soap noodles, (c) an amalgamating step in which the soap noodles are combined with other ingredients of the bar soap composition, (d) a milling step in which a relatively homogeneous mixture is obtained, (e) a plodding step in which the soap mixture is extruded as soap logs and then cut into soap plugs, and (f) a stamping step in which the soap plugs are stamped to yield the finished bar soap composition. Soap noodles used in the following specific examples had the following approximate proportions (%) of soap surfactants (by total weight of the soap noodles): from about 80% to about 90% anhydrous soap, which contained from about 40% to about 50% tallow (TLO), from about 30% to about 45% palm oil stearin (POS), and from about 15% to about 25% palm kernel oil (PKO) or coconut oil (CO).

TABLE 2

Bar Soap Examples

| Ingredient | Bar Ex. 1 | Bar Ex. 2 | Bar Ex. 3 | Bar Ex. 4 |
|---|---|---|---|---|
| Soap Noodle[a] | 74.58% | 78.00% | 77.58% | 75.00% |
| Zinc Pyrithion[b] | 1.00% | 1.00% | 1.00% | 1.00% |
| DTPA[c] | 0.50% | — | 1.00% | — |
| DTPMP[d] 50% solution | — | 0.50% | — | 1.00% |
| Starch[e] | 18.00% | 20.00% | 20.00% | 20.00% |
| TiO$_2$[f] | 0.50% | 0.50% | 0.50% | 0.50% |
| Perfume | 1.10% | 1.10% | 1.10% | 1.10% |
| Water | Q.S. to 100 | Q.S. to 100 | Q.S. to 100 | Q.S. to 100 |
| Moisture Loss | −1.00% | −1.00% | −1.00% | −1.00% |

[a]67.2% tallow soap, about 16.8% coconut soap, about 2% glycerin and about 14% water. These percentage amounts are by weight of the soap noodle.
[b]Zinc Pyrithion sold by Kolon Life Science Inc
[c]Dissolvine DZ sold by Akzo Nobel
[d]Diethylenetriaminepentakis(methylenephosphonic acid), technical ~50% sold by Sigma-Aldrich
[e]NATIONAL CHA501 sold by National Starch and Chemical
[f]MT-500B sold by Tayca Corporation Liquid personal care compositions can be prepared by conventional formulation and mixing techniques.

TABLE 3

Liquid Soap Examples

| Ingredient | Liquid soap Ex. 1 | Liquid soap Ex. 2 | Liquid soap Ex. 3 | Liquid soap Ex. 4 | Liquid soap Ex. 5 | Liquid soap Ex. 6 |
|---|---|---|---|---|---|---|
| Sodium Laureth 3 Sulfate 28% solution[g] | 7.00% | 10.00% | 7.30% | 6.00% | 9.40% | 7.30% |
| Sodium Lauryl Sulfate 29% solution[h] | 2.20% | 4.30% | — | 2.00% | 3.30% | — |
| Cocoamidopropyl Betaine[i] | 1.90% | 2.40% | 3.50% | 0.90% | 1.40% | 3.00% |
| Sodium Benzoate[j] | 0.45% | 0.45% | 0.45% | 0.45% | 0.45% | 0.45% |
| Methylchloroisothiazolinone/ methylisothiazolinone[k] | 0.05% | 0.05% | 0.05% | 0.05% | 0.05% | 0.05% |
| EDTA[l] | 0.10% | 0.10% | 0.10% | 0.10% | 0.10% | 0.10% |
| Fragrance | 0.70% | 0.70% | 0.70% | 0.70% | 0.70% | 0.70% |
| Zinc Pyrithion[m] | 1.00% | 1.00% | 1.00% | 1.00% | 1.00% | 1.00% |
| DTPA[n] | 0.50% | 0.50% | 0.50% | — | — | — |
| DTPMP[p] 50% solution | — | — | — | 1.00% | 1.00% | 1.00% |
| Sodium Chloride[o] | 0-3% | 0-3% | 0-3% | 0-3% | 0-3% | 0-3% |
| Citric acid[p] | Adjust pH | Adjust pH | Adjust pH | Adjust pH | Adjust pH | Adjust pH |
| Purified water | Q.S. to 100 | Q.S. to 100 | Q.S. to 100 | Q.S. to 100 | Q.S. to 100 | Q.S. to 100 |
| pH | 4.50 | 6.00 | 6.00 | 4.50 | 6.00 | 6.00 |

[g]SLE3S sold by Stepan company
[h]SLSS sold by Tianjin Tianzhi Fine Chemical Co., Ltd
[i]AMPHOSOL HCA-HP sold by Stepan
[j]Sodium Benzoate ≥99%, FCG, FG sold by Sigma-Aldrich
[k]Kathon CG sold by Dow Chemical
[l]Obtained from Sigma Aldrich
[m]Zinc Pyrithion sold by Kolon Life Science
[n]Dissolvine DZ sold by Akzo Nobel
[o]Diethylenetriaminepentakis(methylenephosphonic acid), technical ~50% sold by Sigma-Aldrich
[p]Citric acid ACS reagent, ≥99.5% sold by Sigma-Aldrich Cationic Co-Polymer A cationic co-polymer utilized in the present invention can be a random co-polymer comprising monomers selected from the group consisting of acrylamide ("AAM"), dimethyl acrylamide ("DMAA"), acrylamidopropyl trimethylamonium chloride ("APTAC"), methacrylamidopropyl trimethylammonium chloride ("MAPTAC"), and combinations thereof, wherein such cationic co-polymers have a formula:

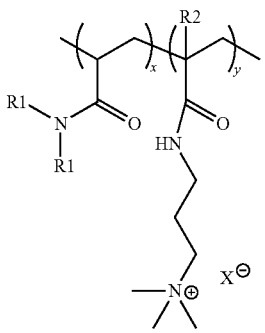

wherein x is an integer selected such that the monomer units constitute less than about 91% by weight of the cationic co-polymer, preferably from 0% to about 91% by weight of the cationic co-polymer, preferably from about 10% to about 85% by weight of the cationic co-polymer, preferably from about 15% to about 60% by weight of the cationic co-polymer, or preferably from about 15% to about 50% by weight of the cationic co-polymer;

y is an integer selected such that the monomer units constitute greater than about 9% by weight of the cationic co-polymer, preferably from 9% to 100% by weight of the cationic co-polymer, preferably from about 15% to about 90% by weight of the cationic co-polymer, preferably from about 40% to about 85% by weight of the cationic co-polymer, or preferably from about 50% to about 85% by weight of the cationic co-polymer;

each R1 is independently selected from the group consisting of H and $CH_3$;

each R2 is independently selected from the group consisting of H and $CH_3$; and $X^-$ is a charge-balancing anion, preferably selected from the group consisting of chloride ion, bromide ion, and iodide ion.

It is believed the effectiveness of the cationic co-polymer as a coating in improving the deposition of microcapsules onto the surface being treated with the consumer product of the present invention is affected by the viscosity of the polymer (as measured according to the VISCOSITY TEST METHOD herein), which relates to the molecular weight of the cationic co-polymer. The effectiveness of the cationic co-polymer as a coating can also be affected by the Water Uptake Value of the cationic co-polymer (as measured by the WATER UPTAKE VALUE TEST METHOD herein), which relates to the gelling capacity of the cationic co-polymer.

The cationic co-polymer of the present invention has a viscosity of at least 0.09 poise, preferably from 0.09 to about 50 poise, preferably from 0.09 to about 25 poise, preferably from about 2 to about 20 poise, preferably from about 2 to about 15 poise, and preferably from about 5 to about 15 poise, as measured by the VISCOSITY TEST METHOD herein.

The number average molecular weight of the cationic co-polymer can be determined according to the MOLECULAR WEIGHT TEST METHOD hereinbelow. The cationic co-polymer of the present invention preferably has a number average molecular weight of from about 10 to about 5,000 kDa (kilodaltons), preferably from about 10 to about 2,500 kDa, preferably from about 20 to about 2,500 kDa, preferably from about 50 to about 2,500 kDa, preferably from about 20 to about 900 kDa, preferably from about 30 to about 500 kDa, and preferably from about 50 to about 300 kDa.

The surface charge of the cationic co-polymer of the present invention is typically cationic and can readily bind to anionically charged surfaces. The cationic co-polymer is generally disposed on the outer surface of the anti-dandruff particles due to a favored adhesion energy between two surfaces. The cationic co-polymer tends to adhere to the outer surface of anti-dandruff particles to form a deformable viscous gel layer. These hydrophobic gels tend to more effectively deposit and adhere to the treated surfaces, such as the treated scalp or the treated skin of a consumer, thereby increasing the deposition of the cationic co-polymer-coated anti-dandruff particles versus anti-dandruff particles that are not coated with cationic co-polymer.

The cationic co-polymer is combined with the anti-dandruff particles, thereby becoming disposed on the outer surface of the anti-dandruff particles, before the anti-dandruff particles are combined with the personal care adjunct ingredients to form the personal care compositions of the present invention.

Cationic co-polymer is preferably incorporated in the present invention in an amount of from about 0.01% to about 8%, preferably from about 0.05% to about 5%, preferably from about 0.1% to about 3%, preferably from about 0.5% to about 1.5%, by weight of the microcapsules.

The cationic co-polymer of the present invention preferably has a Water Uptake Value, as measured by the WATER UPTAKE VALUE TEST METHOD herein, of at least about 2 grams/gram, preferably from about 5 to about 50 g/g, preferably from about 8 to about 40 g/g, preferably from about 10 to about 40 g/g, and preferably from about 15 to about 40 g/g.

A preferred cationic co-polymer has the formula above wherein x is an integer selected such that the monomer units constitute about 40% by weight of the cationic co-polymer and y is an integer selected such that the monomer units constitute about 60% by weight of the cationic co-polymer, R1 is H, and R2 is H. Such a preferred cationic co-polymer has a viscosity of about 10 poise, as measured by the VISCOSITY TEST METHOD herein, and a Water Uptake Value of about 32, as measured by the WATER UPTAKE VALUE TEST METHOD herein. Such a preferred cationic co-polymer is commercially available from Ashland Specialty Chemical Inc. under the trade name N-Hance™ SP-100.

The cationic co-polymer of the present invention is made according to the following general procedure. The desired monomers (AAM, DMAA, APTAC, and/or MAPTAC) are added to a reaction vessel with water. The reaction vessel is sparged with nitrogen to remove oxygen from the system and maintain a nitrogen atmosphere in the reaction vessel. The contents of the reaction vessel are heated to an elevated temperature (e.g. 60° C.) and an initiator solution is added. The contents of the reaction vessel are maintained at elevated temperature for several hours (e.g. 48 hours).

The viscosity and molecular weight of the resulting cationic co-polymer can be impacted by the level of initiator utilized in the reaction vessel. Such initiators can be added to the reaction vessel as 1% or 10% solutions in water, by weight. Suitable initiators include 2.2'-azobis(2-methylpropionamidine) dihydrochloride, available from Wako Chemicals under the trade name V-50.

Anti-Dandruff Agents

The consumer product composition of the present invention comprises an anti-dandruff agent, having an outer surface on which cationic co-polymer is disposed. Anti-dandruff agents can be in the form of a particle and include, but are not limited to, U2 Zinc Pyrithion (length of Particle <2 um, 40% dispersant in water) from Arch Chemicals (Norwalk, Conn.), Azoxystrobin (milled to 2 um size in 5% SLE1S solution) from Jiansu Agrochem Laboratory Co., Ltd (Changzhou, Jiangsu, China), ground Sulfur powder (<45 um) from Solvay & CPC Barium Strontium GmbH & Co. KG (Hans-Böckler-Allee 20•D-30173 Hannover, Germany), piroctone olamine (octopirox) climbazole, and hinokotiol.

Anti-dandruff particles of the present invention will typically have a volume weighted median particle size from about 0.2 microns to about 60 microns, from about 0.3 microns to about 50 microns or from about 0.5 microns to about 45 microns. The volume weighted median particle size of the anti-dandruff particles is determined according to the VOLUME WEIGHTED PARTICLE SIZE TEST METHOD hereinbelow.

Process of Coating Anti-Dandruff Agents

The cationic co-polymer is added to slurries of anti-dandruff particles by mixing the cationic co-polymer with the anti-dandruff particles using a conventional mixing device, such as a spatula, in a conventional mixing container, such as a glass jar. After initial mixing, the mixture is further mixed for several hours in a conventional shaker device at room temperature. On a commercial scale the cationic co-polymer can be added to the anti-dandruff particles via conventional, commercial-scale mixing equipment.

The resulting cationic co-polymer-coated anti-dandruff particles can be combined with personal care adjunct ingredients when the anti-dandruff particles are in one or more forms, including slurry form, neat particle form, and spray dried particle form. The anti-dandruff particles may be combined with the personal care adjunct ingredients by methods that include mixing and/or spraying.

Molecular Weight Test Method

The following test method is used to determine the number average molecular weight of the cationic co-polymer.

Polymer molecular mass is determined by GPC SEC/MALS. The HPLC is a Waters Alliance 2695 HPLC with an auto injector equipped with a bank of two linear μStyragel HT columns at room temperature. The flow rate is 1.0 mL/min and the mobile phase is dimethyl sulfoxide (DMSO) with 0.1% (weight/volume) LiBr. The detectors are Wyatt Dawn EOS Light scattering detectors calibrated with toluene and normalized using 25K dextran in mobile phase and a Wyatt Optilab rEX refractive index detector at 30° C.

Samples for analysis are prepared at a known concentration in the range of 1 to 5 mg/mL. Samples are filtered using 0.2 μm polypropylene membrane filters. The injection volume is 100 μL. The data are collected and analyzed using ASTRA 5.3.4.14. Values for dn/dc are calculated from the RI trace assuming 100% mass recovery. Number average molecular weight and polydispersity index are calculated and reported.

Viscosity Test Method

The following test method is used to determine the viscosity of the cationic co-polymer.

The viscosity of cationic co-polymer test material is determined by measuring a 25° C. 1% (wt/vol) aqueous solution of the cationic co-polymer in deionised (DI) water using a model AR1000 rheometer/viscometer from TA instruments (New Castle, Del., USA). The instrument is configured using parallel steel plates of 60 mm diameter, and a gap size of 500 μm, and a temperature of 25° C. The reported viscosity is the value measured at $1\ s^{-1}$ and at 25° C., during a logarithmic shear rate sweep from $0.06\ s^{-1}$ to $1000\ s^{-1}$ performed during a 1 minute time period.

Water Uptake Value ("WUV") Test Method

The following test method is used to determine the Water Uptake Value ("WUV") of cationic co-polymer.

Polymer test materials are analyzed to determine their capacity to take up or absorb water via the water uptake test method herein. This water uptake adsorption capacity is determined by measuring the weight (in grams) of water uptake per gram of dry polymer test material.

Opened-ended, heat-sealable, empty teabag bags are used to contain samples of the test polymer during exposure to water. These empty teabag bags are made from oxygen-bleached filter paper comprising thermoplastic fibers, abaca fibers, and cellulosic fibers, and have bag dimensions of approximately 5.7 cm×6.4 cm (such as those available from the Special Tea Company, Orlando, Fla., U.S.A. Web: www.specialteacompany.com). Ten empty and dry teabag bags are immersed for 24 hours in hard water having a pH of 7, a calcium carbonate hardness of 154 mg/L, and a temperature between 21° C. and 25° C. After the immersion, the empty tea bags are removed from the water and placed on a dry paper towels for 15 seconds to remove excess moisture via blotting. Each of the 10 empty wet bags is weighed individually with an accuracy of ±0.1 mg and the individual weight results are recorded. These weight data values are averaged to determine the average Empty Wet Bag weight.

A mass of between 300 mg and 600 mg of the dry polymer material being tested is weighed into each of ten dry and labelled open-ended teabags. The weight of each of the ten replicate dry polymer test samples is recorded as an Initial Dry Polymer sample weight, and the open edges of the bags are then heat-sealed to secure the polymer sample inside each bag. Each of the ten polymer-filled bags are then immersed for 24 hours in hard water having a pH of 7, a calcium carbonate hardness of 154 mg/L, and a temperature between 21° C. and 25° C. After the immersion, the bags are removed from the water and placed on a dry paper towel for 15 seconds to remove excess moisture via blotting. Each filled, wet bag is then weighed individually with an accuracy of 0.1 mg and the results are recorded as the individual Filled Wet Bag weights.

The average Empty Wet Bag weight is subtracted from each individual Filled Wet Bag weight to calculate the individual Wet Polymer weight for each of the ten samples. For each of the ten samples, the individual weight of Water Taken Up is calculated by subtracting the Initial Dry Polymer sample weight from the Wet Polymer weight, for each sample respectively. Water Uptake per Gram of Dry Polymer is calculated for each of the ten replicate samples, by dividing the individual weight of Water Taken Up by the individual weight of Initial Dry Polymer, for each respective sample, in accordance with the following three equations:

Filled Wet Bag (g)−average Empty Wet Bag (g)=Wet Polymer (g)

Wet Polymer (g)−Initial Dry Polymer (g)=Water Taken Up (g)

Water Taken Up (g)/Initial Dry Polymer (g)=Water Uptake per Gram of Dry Polymer (g/g)

The Water Uptake Values of the sample polymer are calculated from the ten replicate samples and then averaged. This average result is the value that is reported as the Water Uptake Value in grams of water per gram of dry polymer (in units of grams per gram), for the polymer material being tested.

Volume Weighted Median Particle Size Test Method

The volume weighted median particle size of the microcapsules of the present invention is determined according to the following test method.

The volume weighted median particle size is measured using an Accusizer 780A, made by Particle Sizing Systems, Santa Barbara Calif. The instrument is calibrated from 0 to 300μ using Duke particle size standards. Samples for particle size evaluation are prepared by diluting about 1 g emulsion, if the volume weighted median particle size of the emulsion is to be determined, or 1 g of capsule slurry, if the finished capsule volume weighted median particle size is to be determined, in about 5 g of de-ionized water and further diluting about 1 g of this solution in about 25 g of water.

About 1 g of the most dilute sample is added to the Accusizer and the testing initiated, using the autodilution feature. The Accusizer should be reading in excess of 9200 counts/second. If the counts are less than 9200 additional sample should be added. The accusizer will dilute the test sample until 9200 counts/second and initiate the evaluation. After 2 minutes of testing the Accusizer will display the results, including volume-weighted median size.

The broadness index can be calculated by determining the particle size at which 95% of the cumulative particle volume is exceeded (95% size), the particle size at which 5% of the cumulative particle volume is exceeded (5% size), and the median volume-weighted particle size (50% size-50% of the particle volume both above and below this size). Broadness Index (5)=((95% size)–(5% size)/50% size).

Deposition of Zpt Test Method

The amount of zinc pyrithion (ZPT) deposited onto a substrate by a shampoo is evaluated according to the following test method.

Substrate Preparation: An Innova 42 Shaker was set to 38° C. and allowed to equilibrate. Then artificial sebum (composition shown in TABLE 4) was removed from the refrigerator and place into the Innova 42 Incubator set at 38° C. with occasional shaking until the artificial sebum completely melted. Using a 50 μl pipet 0.05 g of artificial sebum was applied to a Transwell insert membrane being held in the well of a microplate (VWR Tissue Culture Plate Inserts; 6 Well; PC Membrane; 0.4 μm). The lid of the microplate was then placed on to the microplate and the microplate was placed into the preheated Innova 42 Incubator. The microplate was then allowed to sit in the shaker with no shaking for 3 minutes at which point the plate was removed and placed into the freezer for 3 minutes. This heat/cool cycle was repeated twice more. The plate was then allowed to equilibrate at room temperature overnight.

TABLE 4

| Artificial Sebum | |
|---|---|
| Component | Wt % |
| Cholesterol | 2.50 |
| Coconut Fatty Acid | 5.80 |
| Oleic Acid | 19.10 |
| Palmitic Acid | 5.00 |
| Stearic Acid | 2.50 |
| Dodecane | 5.80 |
| Paraffin Oil | 5.00 |
| Squalene | 6.10 |
| Coconut Oil | 19.10 |
| Olive Oil | 21.56 |
| Lanolin | 7.50 |
| Solulan 24 | 0.03 |

Chassis Preparation: Shampoo chassis were prepared with unmodified or co-polymer modified ZPT slurries in a 100 g plastic jar.

Treatment and Deposition Measurement: Then 0.05 g of the shampoo chassis was directly dosed onto the membranes of the six available Transwell plates using a 50 μl pipet. The microplate lid was placed back on the microplate and the microplate was placed in the heated (38° C.) shaker and it was shaken at 150 rpm for 30 second.

The microplate was then removed from the incubator and then 5 mls of tap water was placed into the wells and the microplate placed in the heated (38° C.) incubator where it was shaken at 150 rpm for 30 seconds. This is the first rinse with tap water. The microplate was then removed from the shaker and each of the individual solutions were pipetted off using a plastic pipet and placed into a scintillation vial with lid. The tap water rinse step was repeated twice more (the $2^{nd}$ and the $3^{rd}$ rinses) using fresh tap water each time.

The solution was then transferred to a testing cuvette using a plastic transfer pipette. The cuvette was then placed on a Horiba DUAL FL-UV-800-C fluorometer and running an UV-Vis absorbance scan with the following settings: Excitation Wavelength Start=250; Excitation Wavelength End=800; Excitation Wavelength Increment=3; Integration Time=0.1, and the solutions that were obtained from the chassis only, with no ZPT, were subtracted from the testing samples as background.

Data was analyzed using Aqualog Dual—FL with Origin Software. The process intensity at 335 nm wavelength was selected for data analysis. ZPT concentrations in the rinse solution were calculated based on calibration curves prepared in Tap water solution. Initial Forced Deposition amount of ZPT was known from the amount of chassis placed onto the substrate. We define the deposition 1 amount of ZPT after the first rinse by subtracting the amount of ZPT in the first rinse solution from initial forced deposition amount of ZPT on the substrate. % Deposition 1 after first rinse was defined by dividing deposition 1 amount of ZPT by initial forced deposition amount of ZPT times 100. We define the deposition 2 amount of ZPT after the second rinse by subtracting the amount of ZPT in the second rinse solution from the Deposition 1 amount of ZPT on the substrate. % Deposition 2 after the second rinse was defined by dividing Deposition 2 amount of ZPT by Deposition 1 amount of ZPT times 100. We define the deposition 3 amount of ZPT after the third rinse by subtracting the amount of ZPT in the third rinse solution from the Deposition 2 amount of ZPT on the substrate. % Deposition 3 after the third rinse was defined by dividing deposition 3 amount of ZPT by Deposition 2 amount of ZPT times 100. % Total Deposition after 3 rinse cycles was defined by Deposition 1 times Deposition 2 times Deposition 3 times 100. For data analysis for Azoxystrobin and Sulfur, respectively, the process intensity at 286 nm and 270 nm wavelengths were selected.

The following are examples of microcapsules coated with cationic co-polymer of the present invention, as well as comparative examples of microcapsules coated with cationic co-polymer that is not of the present invention. The cationic co-polymers of Examples C-I, K, N, P, and Q, and Comparative Examples A, B, J, L, M, and O are prepared according to the following synthesis procedure.

Cationic Co-Polymer Synthesis (i) Initiator Solution Preparation 10 ml of water is added to a flask along with 1 gram, or 0.1 gram, of 2,2'-azobis(2-methylpropionamidine) dihydrochloride (available from Wako Chemicals GmbH under the trade name V-50) to form a 10% initiator solution, or a 1% initiator solution, respectively. This 10% initiator solution, or 1% initiator solution, is sparged with argon gas to remove oxygen.

(ii) Polymer Preparation

Into a reaction vessel are added the monomers and water in the appropriate amounts listed for each of the Examples and Comparative Examples in Table 1. The monomers, acrylamide (herein called "AAM"), dimethyl acrylamide (herein called "DMAA"), [3-(acryloylamino)propyl]trimethylammonium chloride (herein called "APTAC") and [3-(methyacryloylamino)propyl]trimethylammonium chloride (herein called "MAPTAC"), are all commercially available from Sigma Aldrich. The reaction vessel is sparged with nitrogen to remove oxygen from the system and a nitrogen atmosphere is maintained in the vessel. The reaction vessel and contents are heated to a temperature of 60° C.

Once the contents have reached 60° C., the 10% initiator solution, or 1% initiator solution, from (i) above is added to the reaction vessel in amounts as specified in Table 1 below (1 milliliter or 0.5 milliliter). The reaction is kept at 60° C. for 48 hours.

The following Table 1 set forth non-limiting examples of cationic co-polymers of the present invention (Ex. C-I, K, N, P, and Q), as well as comparative examples of cationic co-polymers that are not of the present invention (Comp. A, B, J, L, M, and O).

TABLE 5

| Polymer | AAM (g) | DMAA (g) | APTAC (g) | MAPTAC (g) | Water (g) | V50 (ml) 1% Solution | V50 (ml) 10% Solution |
|---|---|---|---|---|---|---|---|
| Comp. A | 8.31 | | 1.70 | | 99.20 | | 1 |
| Comp. B | 6.60 | | 3.40 | | 98.20 | | 1 |
| Ex. C | 6.01 | | 4.01 | | 98.10 | | 1 |
| Ex. D | 4.01 | | 6.01 | | 98.10 | 1 | |
| Ex. E | 6.01 | | 12.20 | | 88.10 | 1 | |
| Ex. F | 1.40 | | 8.60 | | 98.10 | 1 | |
| Ex. G | 0 | | 30.00 | | 80.10 | 1 | |
| Ex. H | 8.31 | | 1.70 | | 99.20 | 1 | |
| Ex. I | 8.85 | | 0.98 | | 98.20 | 1 | |
| Comp. J | 16.79 | | 5.42 | | 88.10 | 1 | |
| Ex. K | | 4.03 | 24.76 | | 76.10 | 0.5 | |
| Comp. L | 8.29 | | | 1.70 | 98.60 | | 1 |
| Comp. M | 6.60 | | | 3.40 | 97.10 | | 1 |
| Ex. N | 6.02 | | | 4.01 | 96.10 | | 1 |
| Comp. O | 9.50 | | | 0.50 | 99.60 | | 1 |
| Ex. P | | 1.99 | | 5.12 | 20.30 | 0.5 | 0.5 |
| Ex. Q | | 7.51 | | 2.50 | 22.88 | 0.5 | |

The viscosity of each cationic co-polymer example and comparative example is measured according to the VISCOSITY TEST METHOD herein. The Water Uptake Value of each cationic co-polymer example and comparative example is measured according to the WATER UPTAKE VALUE TEST METHOD herein. The viscosity and Water Uptake Value of each cationic co-polymer example and comparative example are provided in Table 2 below.

Deposition of ZPT

The co-polymers are used as coatings for ZPT particles as follows. A slurry of U2 Zinc Pyrithion (length of Particle<2 um) particles is obtained from Arch Chemical having 40% solids.

25 g of ZPT slurry was diluted two times using 25 g of millipore water. 50 g of the ZPT slurry and 0.1 g of the co-polymer to be tested was weighed into a glass jar. The slurries contained 1% of Co-polymer to ZPT particles. The jar was then capped, vortex (Fisher Vortex Genie 2, Fisher Scientific; Model #G-560) for 30 sec and then placed onto a shaker (VWR Mini Orbital Shaker; VWR; Model 980125) overnight at room temperature. The resulting co-polymer-coated ZPT particles comprise about 1.0%, by weight of the ZPT particles of co-polymer.

The Shampoo chassis were made by weighing out the amounts of chassis, co-polymer modified ZPT and millipore water listed [In TABLE 1?] into a speedmix jar. The final concentration of ZPT in the chassis was 1%. The materials were then speedmixed at 2750 rpm for 1 min. (DAC-150.1 FVZ-K Speedmixer; FlackTek, Inc.).

The resulting coated ZPT particles were tested for deposition performance according to the DEPOSITION OF ZPT TEST METHOD herein, and the results of such testing are reported in TABLE 6 below for each cationic co-polymer coated ZPTs.

TABLE 6

| Polymer | Ratio of Monomers | Viscosity of 1% PolymerSolution (Poise) | Water Uptake Value (gram of water per gram of polymer) | % Total Deposition |
|---|---|---|---|---|
| | None (ZPTs) | | | 1.00 |
| Comp. A | AAM/ | 83/17 | 0.061 | <0.1 | <1.00 |
| Comp. B | APTAC | 66/34 | 0.072 | <0.1 | <1.00 |
| Ex. C | | 60/40 | 0.091 | 9.8 | 3.32 |
| Ex. D [1] | | 40/60 | 10.570 | 32.5 | 4.42 |
| Ex. E | | 33/67 | 10.53 | 36.35 | 4.45 |
| Ex. F | | 14/86 | 14.2 | 27.53 | 4.50 |
| Ex. G | | 0/100 | 2.948 | 38.7 | 4.31 |
| Ex. H | | 83/17 | 4.342 | 22.55 | 4.35 |
| Ex. I | | 90/10 | 2.657 | 18.71 | 2.95 |
| Comp. J | | 95/5 | 4.000 | 18.03 | <1.00 |
| Ex. K | DMAA/APTAC | 14/86 | 5.699 | 17.53 | 4.40 |
| Comp. L | AAM/ | 83/17 | 0.072 | <0.1 | <1.00 |
| Comp. M | MAPTAC | 66/34 | 0.084 | <0.1 | <1.00 |
| Ex. N | | 60/40 | 0.097 | 8.4 | 3.45 |
| Comp. O | | 95/5 | 0.801 | 17.6 | 1.02 |
| Ex. P | DMAA/ | 28/72 | 7.072 | 39.7 | 3.65 |
| Ex. Q | MAPTAC | 75/25 | 4.788 | 30.35 | 3.55 |

[1] The co-polymer of Example D is commercially available from Ashland Specialty Chemical Inc. under the trade name N-Hance SP-100 ™.

The results provided in TABLE 6 above demonstrate that ZPT coated with the cationic co-polymer of the present invention exhibit improved deposition versus uncoated ZPT or ZPT coated with comparative cationic co-polymer that are not of the present invention.

ZPT coated with the cationic co-polymer of Example D are prepared as indicated above, which contain 0.50%, 1.00%, 1.50%, 5.00% and 6.00%, by weight, of the co-polymer of Example D. The resulting coated ZPT were tested for deposition performance according to the DEPOSITION OF ZPT TEST METHOD herein, and the results of such testing are reported in TABLE 7 below for each cationic co-polymer coated ZPT. The thickness of the coating of co-polymer of Example D on the surface of the ZPT is also reported for each sample.

TABLE 7

| Polymer | % Wt. Polymer to ZPT Particles in the Slurries | Coating Thickness (nm) | % Total Deposition |
|---|---|---|---|
| None (Uncoated ZPT) | 0 | 0 | 1.00 |
| Ex. D | 0.50 | 43 | 4.23 |
| Ex. D | 1.00 | 82 | 4.42 |
| Ex. D | 1.50 | 117 | 9.08 |
| Ex. D | 3.00 | 209 | 3.79 |
| Ex. D | 5.00 | 309 | 2.21 |
| Ex. D | 6.00 | NA (slurries turn to one piece of gel) | <1.0 |

The results provided in TABLE 7 above demonstrate that while increasing levels of cationic co-polymer coating the ZPTs can further improve deposition performance, if too much cationic co-polymer is coated on the ZPTs, it can cause the ZPTs in the slurry to agglomerate into a gel.

The cationic co-polymer of Example D as a coating for ZPTs is compared with further comparative cationic polymers not of the present invention. ZPT particles coated with the cationic co-polymer of Example D, and of the comparative cationic polymers, are prepared as indicated above, containing 1.00%, by weight, of the particular polymer. The resulting coated ZPTs were tested for deposition performance on hair according to the DEPOSITION OF ZPT TEST METHOD herein, and the results of such testing are reported in TABLE 8 below for each cationic polymer coated ZPTs. The Water Uptake Values for each cationic polymer are also provided in TABLE 8 below.

TABLE 8

| Polymer | Water Uptake Value (gram of water per gram of polymer) | % Total Deposition on Hair in Tap Water |
|---|---|---|
| None (Uncoated ZPTs) | NA | 1.00 |
| Ex. D | 32.5 | 4.42 |
| Polyquaternium-7 [1] | <0.1 | <1.00 |
| Polyquaternium-76 [2] | <0.1 | <1.00 |
| Polyquaternium-6 [3] | <0.1 | <1.00 |
| Polyquaternium-74 [4] | <0.1 | <1.00 |

[1] Polyquaternium-7 is commercially available from Solvay under the trade name Mirapol 550 ™.
[2] Polyquaternium-76 is commercially available from Solvay under the trade name Mirapol AT-1 ™.
[3] Polyquaternium-6 is commercially available from Solvay under the trade name Mirapol 100 ™.
[4] Polyquaternium-74 is commercially available from Solvay under the trade name Mirapol PQ-74 ™.

The results provided in TABLE 8 above demonstrate that the structural differences between the cationic co-polymer of the present invention and the comparative cationic polymers, and the resulting difference in Water Uptake Values, can significantly affect the deposition performance of the coated anti-dandruff particles on substrate.

To confirm stability of coated ZPTs in a shampoo solution, shampoo solutions prepared for Ex. D were aged for 2 months at 40° C. and 80% Humidity. No phase separation was observed. Re-testing of the aged samples exhibits the same improvement from the coated ZPTs vs. un-coated ZPTs. This proves co-polymer coatings are stable in a shampoo solution that contains high amounts of surfactants.

The uncoated ZPTs above were also tested according to the DEPOSITION OF ZPT TEST METHOD herein, wherein the cationic co-polymer of Example D was separately added to the shampoo chassis containing the ZPTs at a level of 0.5%, by weight, and at a level of 1.0%, by weight. Such shampoo solutions did not exhibit improved deposition relative to a shampoo solution containing uncoated ZPTs without a cationic co-polymer added. This test demonstrates that separately adding a cationic co-polymer of the present invention to a Shampoo composition containing uncoated ZPTs does not provide a deposition benefit, whereas coating ZPTs with a cationic co-polymer of the present invention, and then adding the coated ZPTs to a shampoo composition, does provide an improvement in deposition performance.

Co-polymer modified Azoxystrobin and Sulfur also showed similar improvements in Deposition as shown for ZPT.

What is claimed is:

1. A personal care composition comprising a personal care adjunct ingredient selected from the group consisting of anionic surfactant, nonionic surfactant, cationic surfactant, a silicone material and mixtures thereof an anti-dandruff agent wherein the anti-dandruff agent is zinc pyrithione present in amount of 1% and having a volume weighted median particle size of from about 0.2 to about 60 microns cationic copolymer coated on an outer surface of zinc pyrithione wherein said cationic co-polymer is formed from the monomers acrylamide and [3-(acryloyl amino)propyl]trimethylammonium chloride and the ratio of monomers acrylamide and [3-(acryloyl amino)propyl]trimethylammonium chloride is 40/60 and the cationic copolymer is present is present in an amount of from about 0.01% to about 6%, by weight, of the zinc pyrithione.

2. The personal care composition of claim 1, wherein said cationic co-polymer has a viscosity of about 10 poise and a Water Uptake Value of about 32 g/g.

3. A method of depositing an anti-dandruff agent on skin or hair, said method comprising the step of
contacting said skin or hair with a personal care composition according to claim 1.

* * * * *